(12) United States Patent
Gropp et al.

(10) Patent No.: US 8,334,399 B2
(45) Date of Patent: Dec. 18, 2012

(54) METHOD FOR PRODUCING ACETONE CYANOHYDRIN AND THE SUBSEQUENT PRODUCTS THEREOF BY SPECIFIC COOLING

(75) Inventors: Udo Gropp, Bad Endorf (DE); Robert Weber, Alsbach-Haehnlein (DE); Thomas Schaefer, Buettelborn (DE); Andreas Perl, Bobenheim-Roxheim (DE); Rudolf Sing, Worms (DE); Thomas Mertz, Bensheim (DE)

(73) Assignee: Evonik Röhm GmbH, Darmstadt (DE)

( * ) Notice: Subject to any disclaimer, the term of this patent is extended or adjusted under 35 U.S.C. 154(b) by 305 days.

(21) Appl. No.: 12/442,123

(22) PCT Filed: Aug. 31, 2007

(86) PCT No.: PCT/EP2007/059092
§ 371 (c)(1),
(2), (4) Date: Mar. 20, 2009

(87) PCT Pub. No.: WO2008/071463
PCT Pub. Date: Jun. 19, 2008

(65) Prior Publication Data
US 2009/0299023 A1 Dec. 3, 2009

(30) Foreign Application Priority Data
Dec. 14, 2006 (DE) .................. 10 2006 059 511

(51) Int. Cl.
C07C 253/00 (2006.01)
C07C 57/02 (2006.01)
C07C 51/08 (2006.01)

(52) U.S. Cl. ........................................ 558/351; 562/398

(58) Field of Classification Search ................... None
See application file for complete search history.

(56) References Cited

U.S. PATENT DOCUMENTS

| | | |
|---|---|---|
| 2,987,542 A | 6/1961 | Modiano |
| 6,180,831 B1 | 1/2001 | Weber et al. |
| 6,596,251 B2 | 7/2003 | Schaefer et al. |
| 6,743,407 B2 | 6/2004 | Schaefer et al. |
| 6,977,310 B2 | 12/2005 | Ackermann et al. |
| 6,979,432 B2 | 12/2005 | Schaefer et al. |
| 7,253,307 B1 | 8/2007 | Carlson, Jr. et al. |
| 7,423,173 B2 | 9/2008 | Krill et al. |
| 7,429,370 B2 | 9/2008 | Von Hippel et al. |
| 2003/0208093 A1 | 11/2003 | Carlson, Jr. et al. |
| 2006/0111586 A1 | 5/2006 | Schladenhauffen et al. |
| 2007/0149811 A1 | 6/2007 | Schleep et al. |
| 2008/0194862 A1 | 8/2008 | Ackermann et al. |
| 2008/0194875 A1 | 8/2008 | Ackermann et al. |
| 2009/0149674 A1 | 6/2009 | Schleep et al. |

FOREIGN PATENT DOCUMENTS

| | | |
|---|---|---|
| EP | 0 035 729 A2 | 9/1981 |
| EP | 1 371 632 | 12/2003 |

OTHER PUBLICATIONS

"Methacrylic Acid and Derivatives", Ullmann's Encyclopedia of Industrial Chemistry, Wiley-VCH Verlag GmbH & Co. KGaA, 1-13, Jun. 15, 2000.*
Salkind et al., Industrial & Engineering Chemistry, 51:1232 (1959).*
U.S. Appl. No. 12/516,629, filed May 28, 2009, Gropp, et al.
U.S. Appl. No. 12/517,366, filed Jun. 3, 2009, Gropp, et al.
U.S. Appl. No. 12/515,545, filed May 20, 2009, Gropp, et al.
U.S. Appl. No. 12/515,964, filed May 22, 2009, Gropp, et al.
U.S. Appl. No. 12/517,673, filed Jun. 4, 2009, Gropp, et al.
U.S. Appl. No. 12/307,773, filed Jan. 7, 2009, Ackermann, et al.
U.S. Appl. No. 12/517,199, filed Jun. 2, 2009, Gropp, et al.
U.S. Appl. No. 12/812,258, filed Jul. 9, 2010, Gropp, et al.
U.S. Appl. No. 12/864,985, filed Jul. 28, 2010, Gropp, et al.
Russian Searh Report issued Jul. 26, 2011, in Patent Application No. 2009 126 613.
Kratkaya Khimicheskaya Enzyklopedia, izdatelstvo Sowjetskaya enziklopedia, Moskwa, 1964, tom 3, str. 127, 188 ("Kurze Chemische Enzyklopadie", Verlag sowjetische Enzyklopädie, Moskau, 1964, vol. 3, S. 127 und 188 (with English-language translation).
Chinese Office Action dated May 3, 2012 in Application No. 200710084385.4 with English translation.

* cited by examiner

*Primary Examiner* — Michael Barker
(74) *Attorney, Agent, or Firm* — Oblon, Spivak, McClelland, Maier & Neustadt, L.L.P.

(57) ABSTRACT

The present invention relates in general terms to a process for preparing acetone cyanohydrin, comprising as steps:
A. contacting acetone and hydrocyanic acid in a reactor to give a reaction mixture, the reaction mixture being circulated, to obtain acetone cyanohydrin;
B. cooling at least some of the reaction mixture by flowing it through a cooling region of a cooler, the cooler including one cooling element or at least two cooling elements;
C. discharging at least a portion of the acetone cyanohydrin obtained from the reactor, the volume of the cooling region of the cooler based on the total internal volume of the cooler being greater than the volume of the cooling element or of the at least two cooling elements of the cooler, to a process for preparing an alkyl methacrylate, to a process for preparing a methacrylic acid, to an apparatus for preparing alkyl methacrylates, to a process for preparing polymers based at least partly on alkyl methacrylates, to the use of the alkyl methacrylates obtainable from the process according to the invention in chemical products, and to chemical products based on the alkyl methacrylates obtainable by the processes according to the invention.

17 Claims, 8 Drawing Sheets

Figure 1:
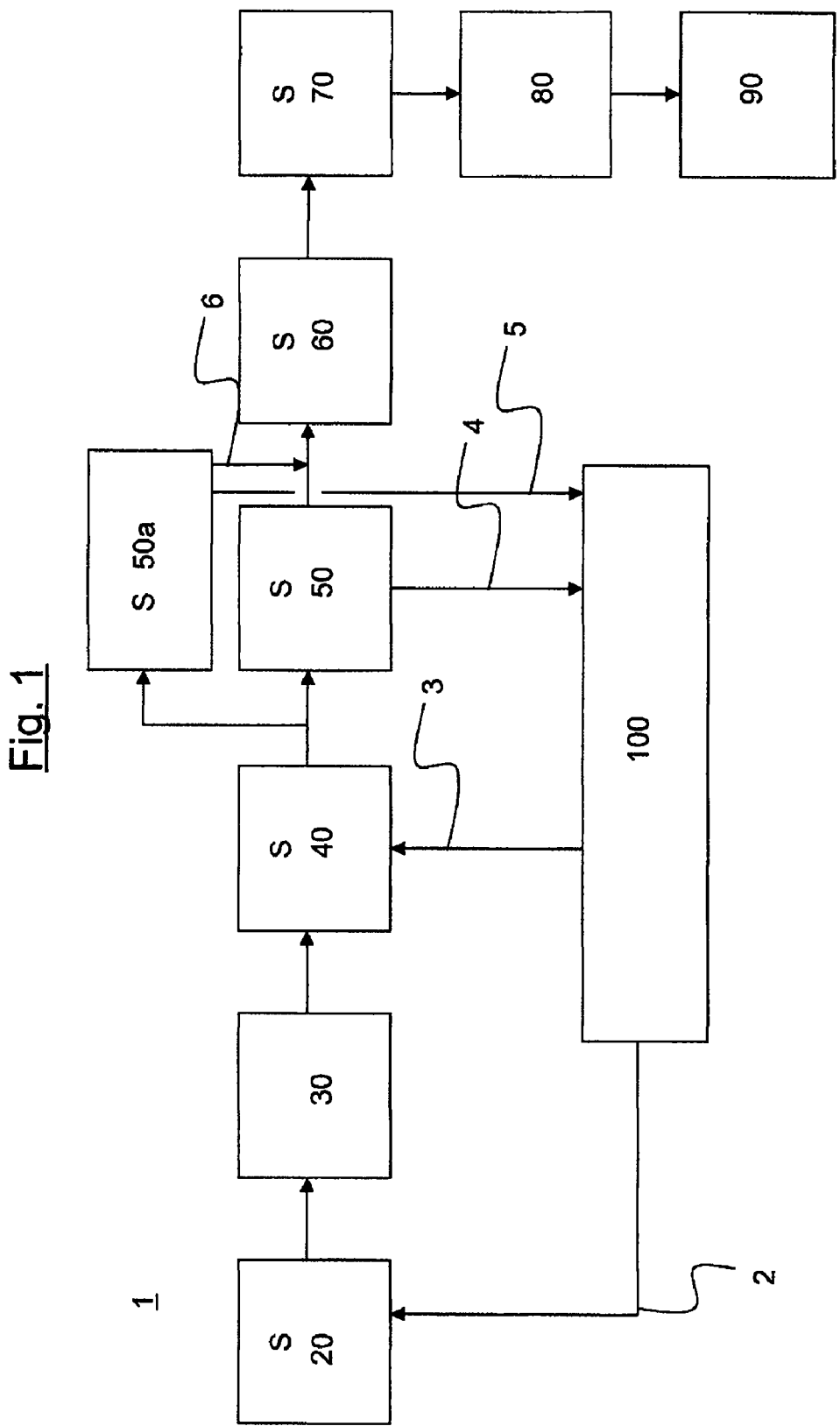

METHOD FOR PRODUCING ACETONE CYANOHYDRIN AND THE SUBSEQUENT PRODUCTS THEREOF BY SPECIFIC COOLING

The present invention relates in general terms to a process for preparing acetone cyanohydrin, to a process for preparing an alkyl methacrylate, to a process for preparing methacrylic acid, to an apparatus for preparing alkyl methacrylates, to a process for preparing polymers based at least partly on alkyl methacrylates, to the use of the alkyl methacrylates obtainable from the process according to the invention in chemical products, and to chemical products based on the alkyl methacrylates obtainable by the processes according to the invention.

Acetone cyanohydrin is one of the important starting components in the preparation of methacrylic acid and alkyl methacrylates. These two compounds are monomers which are of great significance for a number of bulk plastics and whose demand is rising constantly as a result of the increasing rise in the use of these bulk plastics, such that the acetone cyanohydrin starting material is also required in increasingly greater amounts. Acetone cyanohydrin is obtained, for example, from hydrocyanic acid and acetone or else from acetone and hydrocyanic salts. In comparison to acetone, hydrocyanic acid and hydrocyanic salts are significantly more toxic compounds which have to be handled with very great care and hence with a high level of technical safety measures. In order to keep these safety measures within commercially acceptable limits, the conduct of the reaction in the preparation of acetone cyanohydrin is of particular significance. In addition to the general interest in obtaining high yields with minimum reactant concentrations, an additional factor here is the safety interest that, with the acetone cyanohydrin as the product of this reaction, a minimum amount of hydrocyanic acid as the reactant of this reaction be present in the workup of acetone cyanohydrin for further processing.

In the prior art, EP 1 371 632 A1, for example, addresses this safety aspect by a process for preparing acetone cyanohydrin in which a metal cyanide composition is used. This procedure is disadvantageous especially as a result of the metal cyanide intermediate when a plant for preparing hydrocyanic acid and a plant for preparing acetone cyanohydrin are present on the same site, and the hydrocyanic acid prepared can thus be fed directly into the plant for preparing acetone cyanohydrin.

In the present context, there was therefore a general desire to at least partly or even completely eliminate the disadvantages arising from the prior art.

It was a further object of the present invention, by virtue of a maximum conversion, to keep the safety measures which have to be observed in particular in the purification of acetone cyanohydrin as low as possible.

It was a further object of the invention to provide a process for preparing acetone cyanohydrin in which a minimum level of by-products is formed.

In addition, it was an object of the invention to improve the preparation of methacrylic acid or alkyl methacrylates overall, in order thus to obtain a less expensive route to polymers based thereon.

A contribution to the solution of at least one of the above-mentioned objects is made by the subject matter of the category-forming claims, the subclaims dependent thereon constituting preferred embodiments of the present invention.

The present invention thus relates to a process for preparing acetone cyanohydrin, comprising as steps:

A. contacting acetone and hydrocyanic acid in a reactor to give a reaction mixture, the reaction mixture being circulated, to obtain acetone cyanohydrin;

B. cooling at least some, preferably at least 10% by weight, preferentially 50% by weight and more preferably at least 70% by weight, based in each case on the reaction mixture, of the reaction mixture by flowing it through a cooling region of a cooler, the cooler including one cooling element or at least two cooling elements;

C. discharging at least a portion of the acetone cyanohydrin obtained from the reactor, the volume of the cooling region of the cooler based on the total internal volume of the cooler being greater than the volume of the cooling element or of the at least two cooling elements of the cooler.

The reaction mixture can be circulated preferably in a so-called loop reactor, in which the reaction mixture is pumped in circulation, preferably through a pipe system. The flow of the reaction mixture through the cooling region can be effected firstly by virtue of the cooling region directly forming part of the loop reactor. In another embodiment, it is, however, possible that, as well as the circuit of the loop reactor, a cooling region is provided, in which some of the reaction mixture which circulates within the loop reactor is passed in parallel to the loop reactor. In general, the reaction mixture circulates with a volume flow rate in a range of about 30 to about 700 $m^3/h$, preferably in a range of about 100 to about 500 $m^3/h$ and more preferably in a range of about 150 to about 400 $m^3/h$. The flow of the reaction mixture through the cooling region may on the one hand be within the same aforementioned rate ranges. Moreover, it may be preferred for the cooling region to be flowed through within a range of about 10 to 50 times, preferably in a range of about 20 to 40 times and more preferably in a range of about 25 to 35 times by a particular amount of the reaction mixture. In the cooling region, the reaction mixture is brought to a temperature in a range of about 0 to about 50° C., preferably in a range of about 20 to 45° C. and more preferably in a range of about 30 to 40° C. It is desired to keep the reaction mixture substantially isothermal. It is also preferred that, at least in the cooling region, a pressure in a range of about 0.1 to about 10 bar, preferably in a range of about 0.5 to about 5 bar and more preferably in a range of about 0.9 to 1.5 bar is present. It is also preferred that, at least in the cooling region, a pH in a range of about 5 to about 9, preferably in a range of 6 to about 8 and more preferably in a range of about 6.5 to about 7.5 is present.

In general, the cooling region may have any configuration which is known to those skilled in the art and appears to be suitable. For instance, the cooling region of a cooler often has one or at least two cooling elements which ensure the transfer of heat between the medium which is cooling, the reaction mixture here, and the cooling medium present in the cooling element(s). The total internal volume of the cooler generally refers to the volume specified by the manufacturer of the cooler. Often, this volume is the volume of the region in which the heat transfer takes place. Usually, tubes leading to the cooler and leading away from the cooler are not part of the total internal volume of the cooler, since they have no cooling function. The volume of the cooling region is normally determined by subtracting the volume of the cooling element provided in the cooling region or of the cooling elements provided there from the total internal volume of the cooler. The volume of one cooling element is generally greater than the coolant volume capacity of this cooling element, since the components of the cooling element are also taken into account in the determination of its volume. It may be preferred in accordance with the invention that the volume of the cooling region is at least about 1.01 times, preferably at least about 1.1 times and more preferably at least about 1.5 times as great as the volume of the cooling element or of the cooling elements of the cooler.

It is also preferred in the process according to the invention that at least some reaction mixture flows in a cooler flow direction different from the main flow direction at least during the cooling. The main flow direction is determined as the axis between the entry point of the reaction mixture into the cooler and the exit point of the reaction mixture from the cooler. According to the invention, it may be preferred for at least about 5%, preferably at least about 20% and preferentially at least about 40% of the reaction mixture to flow in a cooler flow direction other than the main flow direction within the cooler during the cooling. It is also possible in accordance with the invention that at least one part-stream, preferably at least 10% by volume, preferentially at least 20% by volume and more preferably at least 50% by volume of the reaction mixture fed into the cooling region is conducted past an outer wall which limits the cooling region. This conduct past an outer wall is preferably effected by virtue of circulation streams which preferably extend in spiral form from the entry of the reaction mixture into the cooling region to the exit of the reaction mixture from the cooling region. These flow conditions may either be visualized in a real situation, for example by adding a dye such as fuchsin to threads, or simulated by means of suitable computer programs and mathematical models.

It is also preferred in accordance with the invention that the cooler flow direction is obtained by deflecting the reaction mixture. In turn, it is preferred here that the reaction mixture is deflected by one or at least two deflecting means provided in the cooler or connected to the cooler. In general, these deflecting means may be provided in all regions of the cooler or be connected to the cooler. It may also be preferred that the deflecting means are arranged principally in the region of the cooler in which the reaction mixture enters the cooler with comparatively high flow rate. Thereafter, the deflecting means density decreases starting from the entry region of the reaction mixture to the exit region of the reaction mixture from the cooler.

In principle, useful deflecting means are all devices which are known to those skilled in the art and appear to be suitable. Deflecting means particularly preferred in accordance with the invention are injecting elements, stirring elements or baffle elements, or a combination of at least two thereof.

Useful injecting elements include all devices which are known to those skilled in the art and inject the reaction mixture. These may distribute the reaction mixture within the cooling region firstly by virtue of the pressure of the reaction mixture as passive jets and secondly by virtue of active jets or similar devices. Useful stirring means are likewise all stirrers which are known to those skilled in the art and appear to be suitable, such as paddle stirrers or screw stirrers. Useful baffle elements are in principle also all suitable devices known to those skilled in the art. These are in particular flat internals such as plates, which are known, for example, from static mixers for mixing and distribution. It is preferred that the deflecting means is provided in the cooling region. Thus, the baffle elements in particular may be mounted either on the walls of the cooling region or on the walls of the cooling elements or on both.

Useful cooling elements are all of those which are known in general terms to those skilled in the art and appear to be suitable. It is possible here that the cooling elements are elongated hollow bodies with coolant flow. The cooling elements may have a rod-shaped or plate-shaped configuration. Thus, tube bundle or plate coolers, or a combination of the two, are useful, particular preference being given to tube bundle coolers. In tube bundle coolers, it is also preferred that the deflecting means, preferably designed as baffle elements, are present on the outer wall of the cooler, pointing into the cooling region.

It is also preferred in the process according to the invention that the residence time of the reaction mixture in the cooler is selected such that a minimum level of by-products are formed at maximum conversions to acetone cyanohydrin. For instance, the residence time of the reaction mixture in the cooler is in a range of about 0.1 to about 2 h, preferably in a range of about 0.2 to about 1.5 h and more preferably in a range of about 0.3 to about 1 h.

The present invention further relates to a process for preparing an alkyl methacrylate, comprising as steps:
a. preparing an acetone cyanohydrin by the process according to the invention;
b. contacting the acetone cyanohydrin with an inorganic acid to obtain a methacrylamide;
c. contacting the methacrylamide with an alcohol to obtain an alkyl methacrylate;
d. optionally purifying the alkyl methacrylate.

In addition, the present invention relates to a process for preparing methacrylic acid, comprising as steps:
α) preparing an acetone cyanohydrin by a process according to the invention;
β) contacting the acetone cyanohydrin with an inorganic acid to obtain a methacrylamide;
γ) reacting the methacrylamide with water to give methacrylic acid.

The present invention further relates to an apparatus for preparing alkyl methacrylates, comprising, connected to one another in fluid-conducting form:
   a plant element for preparing acetone cyanohydrin, followed by;
   a plant element for preparing methacrylamide, followed by;
   a plant element for preparing alkyl methacrylate, optionally followed by;
   a plant element for purifying the alkyl methacrylate, optionally followed by;
   a plant element for polymerization, optionally followed by;
   a plant part for finishing,
the plant element for preparing acetone cyanohydrin comprising a loop reactor with a cooler, the cooler comprising a cooling region which can be flowed through and a cooling element. Connected in fluid-conducting form means in the present context that gases, liquids and gas-liquid mixtures or other free-flowing substances can be conducted. In connection with preferred embodiments of the cooler or of the cooling region and also of the cooling element or of the cooling elements, reference is made to the remarks on this subject in this text.

It is also preferred in accordance with the invention that the process according to the invention for preparing an alkyl methacrylate is effected in an inventive apparatus.

The present invention also relates to a process for preparing polymers based at least partly on alkyl methacrylates, comprising the steps of:
A1) preparing an alkyl methacrylate by a process according to the invention;
A2) polymerizing the alkyl methacrylate and optionally a comonomer;
A3) working up the alkyl methacrylate.

Useful comonomers include all of those which are known to those skilled in the art and appear to be suitable, particular preference being given to free-radically polymerizable monomers. Among these, mention should be made in particular of styrene, butyl acrylate or acrylonitrile, methyl acrylate or ethyl acrylate.

Polymerization can be performed as a solution, bead, emulsion or suspension polymerization, or else as a bulk polymerization. The polymer is worked up, for example, by precipitation of the solvent-comprising polymer in a nonsolvent for the polymer as a precipitant. For example, a polymer comprising acetone as the solvent and polymethyl methacrylate is precipitated in a precipitant composed of methanol and water, separated from the precipitant and dried.

In addition, the invention relates to the use of an ultrapure alkyl methacrylate obtainable by the process according to the invention in fibres, films, coatings, moulding compositions, mouldings, papermaking auxiliaries, leather auxiliaries, flocculants and drilling additives as preferred chemical products.

In addition, the invention relates to fibres, films, coatings, moulding compositions, mouldings, papermaking auxiliaries, leather auxiliaries, flocculants and drilling additives as preferred chemical products which are based on a pure methacrylic ester obtainable by the process according to the invention.

Various process elements and plant parts will be illustrated hereinafter, which can in principle be combined with the present invention individually or as an ensemble of two or more of the process elements mentioned. In some cases, it may be advantageous when the process elements presented within the present text are combined with the present invention such that they are combined overall to give a process for preparing esters of methacrylic acid or a process for preparing methacrylic acid. However, it should also be pointed out that advantageous effects can usually also be achieved when the subject matter of the present invention as such is used in another field or only combined with some of the process elements presented here.

Preparation of Acetone Cyanohydrin

In this process element, acetone cyanohydrin is prepared by commonly known processes (see, for example, Ullmann's Enzyklopädie der technischen Chemie, 4th Edition, Volume 7). Frequently, the reactants used are acetone and hydrocyanic acid. The reaction is an exothermic reaction. In order to counteract decomposition of the acetone cyanohydrin formed in this reaction, the heat of reaction is typically removed by a suitable apparatus. The reaction can be conducted in principle as a batch process or as a continuous process; when a continuous process is preferred, the reaction is frequently performed in a loop reactor which is fitted out appropriately.

A main feature of a method leading to the desired product in high yields is often that the reaction product is cooled at sufficient reaction time and the reaction equilibrium is shifted in the direction of the reaction product. In addition, the reaction product is frequently admixed with an appropriate stabilizer to the advantage of the overall yield, in order to prevent decomposition in the course of the later workup to give the starting materials.

The mixing of the acetone and hydrocyanic acid reactants can in principle be effected in essentially any way. The method of mixing depends in particular on whether a batchwise mode, for example in a batch reactor, or a continuous mode, for example in a loop reactor, is selected.

In principle, it may be advantageous when the acetone is fed into the reaction via a reservoir vessel which has a scrubber tower. Venting lines which conduct waste air containing acetone and hydrocyanic acid can thus be conducted, for example, through this reservoir vessel. In the scrubbing tower which is attached to the reservoir vessel, the waste air escaping from the reservoir vessel can be scrubbed with acetone, which removes hydrocyanic acid from the waste air and recycles it into the process. For this purpose, for example, some of the amount of acetone introduced from the reservoir vessel into the reaction is conducted in the part-stream through a cooler, preferably through a brine cooler, into the top of the scrubbing tower and the desired result is thus achieved.

Depending on the size of the amount of end products to be produced, it may be advantageous to feed the acetone to the reaction from more than just one reservoir vessel. In this context, it is possible for each of the two or more reservoir vessels to bear a corresponding scrubbing tower. However, it is in many cases sufficient when only one of the reservoir vessels is equipped with a corresponding scrubbing tower. In this case, it is, however, often advisable for corresponding lines which conduct waste air and can transport acetone and hydrocyanic acid to be conducted through this vessel or through this scrubbing tower.

The temperature of the acetone in the reservoir may in principle be within an essentially arbitrary range, provided that the acetone is in the liquid state at the appropriate temperature. The temperature in the reservoir vessel is advantageously, however, about 0 to about 20° C.

In the scrubbing tower, the acetone used for scrubbing is cooled by means of an appropriate cooler, for example by means of a plate cooler, with brine to a temperature of about 0 to about 10° C. The temperature of the acetone on entry into the scrubbing tower is therefore preferably, for example, about 2 to about 6° C.

The hydrocyanic acid required in the reaction can be introduced into the reactor either in liquid or in gaseous form. It may, for example, be crude gas from the BMA process or from the Andrussow process.

The hydrogen cyanide can, for example, be liquefied, for example by the use of an appropriate cooling brine. Instead of liquefied hydrocyanic acid, coking oven gas can be used. For example, hydrogen cyanide-containing coking oven gases, after scrubbing with potash, are scrubbed continuously in countercurrent with acetone which contains 10% water, and the reaction to give acetone cyanohydrin can be carried out in the presence of a basic catalyst in two gas scrubbing columns connected in series.

In a further embodiment, a gas mixture comprising hydrogen cyanide and inert gases, especially a crude gas from the BMA process or from the Andrussow process, can be reacted with acetone in the presence of a basic catalyst and acetone cyanohydrin in a gas-liquid reactor.

In the process described here, preference is given to using a BMA crude gas or an Andrussow crude gas. The gas mixture resulting from the abovementioned customary processes for preparing hydrogen cyanide can be used as such or after an acid scrubbing. The crude gas from the BMA process, in which essentially hydrocyanic acid and hydrogen are formed from methane and ammonia, contains typically 22.9% by volume of HCN, 71.8% by volume of $H_2$, 2.5% by volume of $NH_3$, 1.1% by volume of $N_2$, 1.7% by volume of $CH_4$. In the known Andrussow process, hydrocyanic acid and water are formed from methane and ammonia and atmospheric oxygen. The crude gas of the Andrussow process, when oxygen is used as the oxygen source, contains typically 8% by volume of HCN, 22% by volume of $H_2O$, 46.5% by volume of $N_2$, 15% by volume of $H_2$, 5% by volume of CO, 2.5% by volume of $NH_3$ and 0.5% by volume each of $CH_4$ and $CO_2$.

When a non-acid-scrubbed crude gas from the BMA process or Andrussow process is used, the ammonia present in the crude gas frequently acts as a catalyst for the reaction. Since the ammonia present in the crude gas frequently exceeds the amount required as a catalyst and can therefore lead to high losses of sulphuric acid used for stabilization, such a crude gas is often subjected to an acid scrubbing in order to eliminate ammonia therefrom. When such an acid-scrubbed crude gas is used, it is then necessary, however, to add a suitable basic catalyst to the reactor in a catalytic amount. In principle, known inorganic or organic basic compounds may function as the catalyst.

Hydrogen cyanide in gaseous or in liquid form, or a gas mixture comprising hydrogen cyanide, and acetone are fed continually to a loop reactor in the continuous mode. In this case, the loop reactor comprises at least one means of feeding acetone or two or more such means, at least one means for feeding liquid or gaseous hydrocyanic acid, or two or more such means, and at least one means for feeding a catalyst.

Suitable catalysts are in principle any alkaline compounds, such as ammonia, sodium hydroxide solution or potassium hydroxide solution, which can catalyse the reaction of acetone and hydrocyanic acid to give acetone cyanohydrin. However, it has also been found to be advantageous when the catalyst used is an organic catalyst, especially an amine. Suitable examples are secondary or tertiary amines such as diethylamine, dipropylamine, triethylamine, tri-n-propylamine and the like.

A loop reactor useable in the process element described further comprises at least one pump, or two or more pumps, and at least one mixing apparatus, or two or more such mixing apparatuses.

Suitable pumps are in principle all pumps which are suitable for ensuring the circulation of the reaction mixture in the loop reactor.

Suitable mixing apparatuses are both mixing apparatuses with mobile elements and so-called static mixers in which immobile flow resistances are provided. In the case of use of static mixers, suitable examples are those which allow an operational transfer of at least about 10 bar, for example at least about 15 bar or at least about 20 bar under operating conditions without significant restrictions in the functioning. Appropriate mixers may consist of plastic or metal.

Suitable plastics are, for example, PVC, PP; HDPE, PVDF, PVA or PTFE. Metal mixers may consist, for example, of nickel alloys, zirconium, titanium and the like. Likewise suitable are, for example, rectangular mixers.

The catalyst is added in the loop reactor preferably downstream of the pump and upstream of a mixing element present in the loop reactor. In the reaction described, catalysts are used, for example, in such an amount that the overall reaction is conducted at a pH of not more than 8, in particular not more than about 7.5 or about 7. It may be preferred when the pH in the reaction varies within a range of about 6.5 to about 7.5, for example about 6.8 to about 7.2.

Alternatively to the addition of the catalyst into the loop reactor downstream of the pump and upstream of a mixing apparatus, it is also possible in the process described to feed the catalyst into the loop reactor together with the acetone. In such a case, it may be advantageous when appropriate mixing of acetone and catalyst is ensured before feeding into the loop reactor. Appropriate mixing can be effected, for example, by the use of a mixer with moving parts or by use of a static mixer.

When a continuous process in a loop reactor is selected as the operating mode in the process described, it may be appropriate to examine the state of the reaction mixture by instantaneous or continual analyses. This offers the advantage that, where appropriate, it is also possible to react rapidly to changes in state in the reaction mixture. Furthermore, it is thus possible, for example, to meter in the reactants very precisely in order to minimize yield losses.

Corresponding analysis can be effected, for example, by sampling in the reactor loop. Suitable analysis methods are, for example, pH measurement, measurement of the exothermicity or measurement of the composition of the reaction mixture by suitable spectroscopic processes.

Especially within the context of conversion monitoring, quality aspects and safety, it has been found to be useful to determine the conversion in the reaction mixture via the heat removed from the reaction mixture and to compare it with the heat which is released theoretically.

In the case of suitable selection of the loop reactor, the actual reaction can in principle be effected within the tube systems arranged within the loop reactor. Since the reaction, however, is exothermic, in order to avoid yield loss, sufficient cooling and sufficient removal of the heat of reaction should be ensured. It has frequently been found to be advantageous when the reaction proceeds within a heat exchanger, preferably within a tube bundle heat exchanger. Depending on the amount of product to be produced, the capacity of an appropriate heat exchanger can be selected differently. For industrial scale processes, heat exchangers having a volume of about 10 to about 40 $m^3$ in particular have been found to be particularly suitable. The tube bundle heat exchangers used with preference are heat exchangers which have a tube bundle flowed through by liquid within a jacket flowed through by liquid. Depending on the tube diameter, packing density, etc., the heat transfer between the two liquids can be adjusted appropriately. It is possible in principle in the process described to conduct the reaction to the effect that the reaction mixture is conducted through the heat exchanger in the tube bundle itself and the reaction takes place within the tube bundle, the heat being removed from the tube bundle into the jacket liquid.

However, it has likewise been found to be practicable and in many cases to be viable to conduct the reaction mixture through the jacket of the heat exchanger, while the liquid used for cooling is circulated within the tube bundle. It has in many cases been found to be advantageous when the reaction mixture is distributed within the jacket by means of flow resistances, preferably deflecting plates, to achieve a higher residence time and better mixing.

The ratio of jacket volume to the volume of the tube bundle may, depending on the design of the reactor, be about 10:1 to about 1:10; the volume of the jacket is preferably greater than the volume of the tube bundle (based on the contents of the tubes).

The heat removal from the reactor is adjusted with an appropriate coolant, for example with water, such that the reaction temperature is within a corridor of about 25 to about 45° C., in particular about 30 to about 38° C., in particular about 33 to about 35° C.

A product is removed continuously from the loop reactor. The product has a temperature within the abovementioned reaction temperatures, for example a temperature of about 35° C. The product is cooled by means of one or more heat exchangers, especially by means of one or more plate heat exchangers. For example, brine cooling is used. The temperature of the product after cooling should be about 0 to 10° C., in particular 1 to about 5° C. The product is preferably transferred into a storage vessel which has a buffer function. In addition, the product in the storage vessel can be cooled further, for example, by constantly removing a part-stream from the storage vessel to a suitable heat exchanger, for example to a plate heat exchanger, or kept at a suitable storage temperature. It is entirely possible that continued reaction can take place in the storage vessel.

The product can be recycled into the storage vessel in any way in principle. However, it has been found to be advantageous in some cases that the product is recycled by means of a system composed of one or more nozzles into the storage vessel such that corresponding mixing of the stored product takes place within the storage vessel.

Product is also removed continuously from the storage vessel into a stabilization vessel. The product is admixed there with a suitable acid, for example with $H_2SO_4$. This deactivates the catalyst and adjusts the reaction mixture to a pH of about 1 to about 3, in particular about 2. A suitable acid is in particular sulphuric acid, for example sulphuric acid having a content of about 90 to about 105%, in particular of about 93 to about 98% $H_2SO_4$.

The stabilized product is withdrawn from the stabilization vessel and transferred into the purification stage. A portion of the stabilized product withdrawn can be recycled, for example, into the stabilization vessel such that sufficient mixing of the vessel is ensured by means of a system composed of one or more nozzles.

ACH Workup

In a further process element which can be used in connection with the present invention, acetone cyanohydrin which has been obtained in a preceding stage, for example from the reaction of acetone with hydrocyanic acid, is subjected to a distillative workup. The stabilized crude acetone cyanohydrin is freed of low-boiling constituents by means of a corresponding column. A suitable distillation process can be conducted, for example, by means of only one column. However, it is likewise possible, in an appropriate purification of crude acetone cyanohydrin, to use a combination of two or more distillation columns, also combined with a falling-film evaporator. In addition, two or more falling-film evaporators or else two or more distillation columns may be combined with one another.

The crude acetone cyanohydrin comes from the storage to the distillation generally with a temperature of about 0 to about 15° C., for example a temperature of about 5 to about 10° C. In principle, the crude acetone cyanohydrin can be introduced directly into the column. However, it has been found to be useful in some cases when the crude cool acetone cyanohydrin, by means of a heat exchanger, first takes up some of the heat of the product already purified by distillation. Therefore, in a further embodiment of the process described here, the crude acetone cyanohydrin is heated by means of a heat exchanger to a temperature of about 60 to 80° C.

The acetone cyanohydrin is purified by distillation by means of a distillation column, preferably having more than 10 trays, or by means of a battery of two or more corresponding suitable distillation columns. The column bottom is heated preferably with steam. It has been found to be advantageous when the bottom temperature does not exceed a temperature of 140° C.; good yields and good purification have been achieved when the bottom temperature is not greater than about 130° C. or not higher than about 110° C. The temperature data are based on the wall temperature of the column bottom.

The crude acetone cyanohydrin is fed to the column body in the upper third of the column. The distillation is performed preferably under reduced pressure, preferably at a pressure of about 50 to about 900 mbar, in particular about 50 to about 250 mbar and with good results between 50 and about 150 mbar.

At the top of the column, gaseous impurities, especially acetone and hydrocyanic acid, are removed, the removed gaseous substances are cooled by means of one heat exchanger or a battery of two or more heat exchangers. Preference is given here to using brine cooling with a temperature of about 0 to about 10° C. This gives the gaseous constituents of the vapours the opportunity to condense. The first condensation stage may take place, for example, at standard pressure. However, it is equally possible and has been found to be advantageous in some cases when this first condensation stage is effected under reduced pressure, preferably at the pressure which prevails in the distillation. The condensate is passed on into a cooled collecting vessel and collected there at a temperature of about 0 to about 15° C., in particular at about 5 to about 10° C.

The gaseous compounds which do not condense in the first condensation step are removed from the reduced pressure chamber by means of a vacuum pump. In principle, any vacuum pump can be used here. However, it has been found to be advantageous in many cases to use a vacuum pump which, owing to its design, does not lead to the introduction of liquid impurities into the gas stream. Preference is therefore given here, for example, to using dry-running vacuum pumps.

The gas stream which escapes on the pressure side of the pump is conducted through a further heat exchanger which is preferably cooled with brine at a temperature of about 0 to about 15° C. Constituents which condense here are likewise collected in the collecting vessel which already collects the condensates obtained under vacuum conditions. The condensation performed on the pressure side of the vacuum pump can be effected, for example, by a heat exchanger, but also with a battery of two or more heat exchangers arranged in series or in parallel. Gaseous substances remaining after this condensation step are removed and sent to any further utilization, for example a thermal utilization.

The collected concentrates may likewise be utilized further as desired. However, for economic reasons, it has been found to be extremely advantageous to recycle the condensates into the reaction for preparing acetone cyanohydrin. This is effected preferably at one or more points which enable access to the loop reactor. The condensates may in principle have any composition provided that they do not disrupt the preparation of the acetone cyanohydrin. In many cases, a predominant amount of the condensate will, however, consist of acetone and hydrocyanic acid, for example in a molar ratio of about 2:1 to about 1:2, frequently in a ratio of about 1:1.

The acetone cyanohydrin obtained from the bottom of the distillation column is first cooled to a temperature of about 40 to about 80° C. by the cold crude acetone cyanohydrin fed in by means of a first heat exchanger. Subsequently, the acetone cyanohydrin is cooled to a temperature of about 30 to about 35° C. by means of at least one further heat exchanger and optionally stored intermediately.

Amidation

In a further process element as frequently provided in the preparation of methacrylic acid or of esters of methacrylic acid, acetone cyanohydrin is subjected to a hydrolysis. At different temperature levels after a series of reactions, this forms methacrylamide as the product.

The reaction is brought about in a manner known to those skilled in the art by a reaction between concentrated sulphuric acid and acetone cyanohydrin. The reaction is exothermic, which means that heat of reaction is advantageously removed from the system.

The reaction here too can again be performed in a batchwise process or in continuous processes. The latter has been found to be advantageous in many cases. When the reaction is performed in a continuous process, the use of loop reactors has been found to be useful. The reaction can be effected, for example, in only one loop reactor. However, it may be advantageous when the reaction is performed in a battery of two or more loop reactors.

In the process described, a suitable loop reactor has one or more feed points for acetone cyanohydrin, one or more feed points for concentrated sulphuric acid, one or more gas separators, one or more heat exchangers and one or more mixers, and often a pump as a conveying means.

The hydrolysis of acetone cyanohydrin with sulphuric acid to give methacrylamide is, as already described, exothermic. The heat of reaction which arises in the reaction must, however, at least largely be withdrawn from the system, since the yield falls with increasing temperature in the reaction. It is possible in principle to achieve a rapid and comprehensive removal of the heat of reaction with appropriate heat exchangers. However, it may also be disadvantageous to cool the mixture too greatly, since a sufficient heat transfer is required for appropriate exchange at the heat exchangers. Since the viscosity of the mixture rises greatly with falling temperature, the circulation in and the flow through the loop reactor is firstly complicated, and sufficient removal of the reaction energy from the system can secondly no longer be ensured.

In addition, excessively low temperatures in the reaction mixture can lead to a crystallization of constituents of the reaction mixture at the heat exchangers. This further worsens the heat transfer, as a result of which a clear yield reduction can be detected. In addition, the loop reactor cannot be charged with the optimal amounts of reactants, such that the efficiency of the process suffers overall.

In one embodiment of the process, a portion, preferably about two thirds to about three quarters, of the volume flow rate from a stream of acetone cyanohydrin is introduced into a first loop reactor. A first loop reactor preferably has one or more heat exchangers, one or more pumps, one or more mixing elements and one or more gas separators. The circulation streams which pass through the first loop reactor are preferably in the range of about 50 to 650 m³/h, preferably in a range of 100 to 500 m³/h and more preferably in a range of about 150 to 450 m³/h. In an at least one further loop reactor which follows the first loop reactor, the circulation streams are preferably in a range of about 40 to 650 m³/h, preferably in a range of 50 to 500 m³/h and more preferably in a range of about 60 to 350 m³/h. Moreover, a preferred temperature difference over the heat exchangers is about 1 to 20° C., particular preference being given to about 2 to 7° C.

The acetone cyanohydrin can in principle be fed into the loop reactor at any point. However, it has been found to be advantageous when the feed is into a mixing element, for example into a mixer with moving parts or a static mixer, or at a well-mixed point. The sulphuric acid is advantageously fed in upstream of the acetone cyanohydrin addition. Otherwise, it is, however, likewise possible to feed the sulphuric acid into the loop reactor at any point.

The ratio of the reactants in the loop reactor is controlled such that an excess of sulphuric acid is present. The excess of sulphuric acid is, based on the molar ratio of the constituents, about 1.8:1 to about 3:1 in the first loop reactor and about 1.3:1 to about 2:1 in the last loop reactor.

In some cases, it has been found to be advantageous to perform the reaction in the loop reactor with such an excess of sulphuric acid. The sulphuric acid may serve here, for example, as a solvent and keep the viscosity of the reaction mixture low, which can ensure a higher removal of heat of reaction and a lower temperature of the reaction mixture. This can entail significant yield advantages. The temperature in the reaction mixture is about 90 to about 120° C.

The heat removal is ensured by one or more heat exchangers in the loop reactor. It has been found to be advantageous when the heat exchangers have a suitable sensor system for controlling the cooling performance in order to prevent excessively great cooling of the reaction mixture for the aforementioned reasons. For example, it may be advantageous to measure the heat transfer in the heat exchanger or in the heat exchangers point by point or continuously and to adjust the cooling performance of the heat exchangers thereto. This can be done, for example, via the coolant itself. It is equally possible to achieve appropriate heating of the reaction mixture by corresponding variation of the addition of the reactants and by the generation of more heat of reaction. A combination of the two possibilities is also conceivable. The loop reactor should additionally have at least one gas separator. One method is to withdraw product formed continuously from the loop reactor via the gas separator. Another method is thus to withdraw the gases formed in the reaction from the reaction chamber. The gas formed is mainly carbon monoxide. The product withdrawn from the loop reactor is preferably transferred into a second loop reactor. In this second loop reactor, the reaction mixture comprising sulphuric acid and methacrylamide, as has been obtained by the reaction in the first loop reactor, is reacted with the remaining part-stream of acetone cyanohydrin. In this case, the excess of sulphuric acid from the first loop reactor, or at least some of the excess sulphuric acid, reacts with the acetone cyanohydrin to form further methacrylamide. The performance of the reaction in two or more loop reactors has the advantage that, owing to the sulphuric acid excess in the first loop reactor, the pumpability of the reaction mixture and hence the heat transfer and ultimately the yield are improved. In turn, at least one mixing element, at least one heat exchanger and at least one gas separator are arranged in the second loop reactor. The reaction temperature in the second loop reactor is likewise about 90 to about 120° C.

The problem of the pumpability of the reaction mixture, of heat transfer and of a minimum reaction temperature occurs in every further loop reactor just as it does in the first. Therefore, the second loop reactor too advantageously has a heat exchanger whose cooling performance can be controlled by an appropriate sensor system.

The acetone cyanohydrin is again fed in a suitable mixing element, preferably into a static mixer or at a well-mixed point.

The product is withdrawn from the separator, especially gas separator, of the second loop reactor and heated to a temperature of about 130 to about 180° C. to complete the reaction and to form the methacrylamide.

The heating is preferably performed such that the maximum temperature is attained only for a minimum period, for example for a time of about one minute to about 30 minutes, in particular for a time of about two to about eight or about three to about five minutes. This can in principle be effected in any apparatus for achieving such a temperature for such a short period. For example, the energy can be supplied in a conventional manner by electrical energy or by steam. However, it is equally possible to supply the energy by means of electromagnetic radiation, for example by means of microwaves.

In various cases, it has been found to be advantageous when the heating step is effected in a heat exchanger with two-stage or multistage arrangement of tube coils which may preferably be present in an at least double, opposite arrangement. This heats the reaction mixture rapidly to a temperature of about 130 to 180° C.

The heat exchanger can be combined, for example, with one or more gas separators. For example, it is possible to conduct the reaction mixture through a gas separator after it leaves the first tube coil in the heat exchanger. This can remove, for example, gaseous components formed during the reaction from the reaction mixture. It is equally possible to treat the reaction mixture with a gas separator after it leaves the second coil. It may additionally be found to be advantageous to treat the reaction mixture with a gas separator both after it leaves the first tube coil and after it leaves the second tube coil.

The amide solution thus obtainable generally has a temperature of more than 100° C., typically a temperature of about 130 to 180° C.

The gaseous compounds obtained in the amidation can in principle be disposed of in any way or sent to further processing. However, it may be advantageous in some cases when the appropriate gases are combined in a transport line in such a way that they are optionally pressurized either continuously or as required, for example with steam pressure, and can thus be transported further.

Esterification

A further step which constitutes a process element and can be used in the present invention in connection with the process according to the invention is a hydrolysis of methacrylamide to methacrylic acid and its subsequent esterification to methacrylic esters. This reaction can be performed in one or more heated, for example steam-heated, tanks. However, it has in many cases been found to be advantageous when the esterification is performed in at least two successive tanks, but, for example, also in three or four or more successive tanks. In this case, a solution of methacrylamide is introduced into the tank or into the first tank of a battery of tanks comprising two or more tanks.

It is frequently preferred to perform a corresponding esterification reaction with a battery of two or more tanks. Reference will therefore be made hereinafter exclusively to this variant.

In the process described here, it is possible, for example, to feed an amide solution as obtainable from the amidation reaction described here into a first tank. The tank is heated, for example, with steam. The amide solution supplied generally has an elevated temperature, for example a temperature of about 100 to about 180° C., essentially corresponding to the exit temperature of the amide solution from the amidation reaction presented above. An alkanol is also fed to the tanks, which can be used for the esterification.

Suitable alkanols here are in principle any alkanols having 1 to about 4 carbon atoms, which may be linear or branched, saturated or unsaturated, particular preference being given to methanol. These alkanols may likewise be used together with methacrylic esters, which is the case especially in transesterifications.

The tank is also charged with water, so that there is a total water concentration in the tank of about 13 to about 26% by weight, in particular about 18 to about 20% by weight.

The amount of amide solution and of alkanol is controlled such that a total molar ratio of amide to alkanol of about 1:1.4 to about 1:1.6 exists. The alkanol can be distributed over the tank battery such that the molar ratio in the first reactor is about 1:1.1 to about 1:1.4 and, in the subsequent reaction stages, based on the total amide stream, molar ratios of about 1:0.05 to about 1:0.3 are established. The alkanol fed into the esterification may be composed of "fresh alkanol" and alkanol from recycling streams of the workup stages and, if required, also of recycling streams of the downstream processes of the production system.

The first tank can be charged with water in principle such that water is fed to the tank from any source, provided that this water has no ingredients which might adversely affect the esterification reaction or the downstream process stages. For example, demineralized water or spring water can be fed to the tank. However, it is likewise possible to feed a mixture of water and organic compounds to the tank, as obtained, for example, in the purification of methacrylic acid or methacrylic esters. In a preferred embodiment of the process presented here, the tank is charged at least partly with a mixture of water and such organic compounds.

When a battery of two or more tanks is used in the esterification reaction, the gaseous substances formed, especially the methacrylic esters, can in principle be drawn off individually from each tank and fed to a purification. However, it has been found in some cases to be advantageous when, in a battery of two or more tanks, the gaseous products from the first tank are first fed into the second reaction vessel without the gaseous compounds from the first tank being fed directly to a purification. This procedure offers the advantage that the frequently high evolution of foam in the first tank need not be counteracted by complicated defoaming apparatus. In the case of passage of the gaseous substances from the first tank into the second tank, the foam which has been formed in the first tank and may have been entrained also enters the reaction chamber of the second tank in a simple manner. Since the foam formation there is generally significantly lower, there is no need to use defoaming apparatus.

The second tank arranged downstream of a first tank then firstly takes up the overflow of the first tank; secondly, it is fed with the gaseous substances formed in the first tank or which are present in the first tank. The second tank and any following tanks are likewise charged with methanol. It is preferred here that the amount of methanol decreases by at least 10% from tank to tank, based in each case on the preceding tank. The water concentration in the second tank and in the further tanks may differ from that of the first tank; the concentration differences are, though, often small.

The vapours formed in the second tank are removed from the tank and introduced into the bottom of a distillation column.

When the esterification is performed with a battery of three or more tanks, the overflow of the second tank is transferred in each case into a third tank, and the overflow of the third tank, if appropriate, into a fourth tank. The further tanks are likewise steam-heated. The temperature in tanks 3 and, if appropriate, 4 is preferably adjusted to about 120 to about 140° C.

The vapours escaping from the tanks are passed into a distillation column, this preferably being effected in the lower region of the distillation column. The vapours comprise an azeotropic mixture of carrier steam, methacrylic esters and alkanol and, depending on the alkanol used, have a temperature of about 60 to about 120° C., for example about 70 to about 90° C., when methanol is used. In the distillation column, the methacrylic ester is separated in gaseous form from the vapour constituents which boil at higher temperatures. The high-boiling fractions (mainly methacrylic acid, hydroxyisobutyric esters and water) are recycled into the first reaction tank. The methacrylic ester formed is drawn off at the top of the column and cooled by means of a heat exchanger or a battery of two or more heat exchangers. It has been found to be useful in some cases when the methacrylic ester is cooled by means of at least two heat exchangers, in which case a first heat exchanger with water performs the condensation and a cooling to a temperature of about 60 to about 30° C., while a second brine-cooled heat exchanger undertakes a cooling to about 5 to about 15° C. A part-stream from the water-cooled condensate can be introduced as reflux to the columns for concentration control in the column. However, it is equally possible to cool the methacrylic ester formed by means of a battery of more than two heat exchangers. In this case, it is possible, for example, first to undertake a cooling by means of two water-cooled heat exchangers connected in series and then to achieve a further cooling by means of an appropriate brine-cooled heat exchanger.

For example, in the process presented here, the methacrylic ester formed can be cooled in the gaseous state by means of a first heat exchanger with water cooling. Both condensed and uncondensed substances are then passed on into a second heat exchanger, where a further condensation by means of water cooling takes place. At this point, for example, gaseous substances can then be transferred into a separate brine-cooled heat exchanger. The condensate in this brine-cooled heat exchanger is then introduced into the distillate stream, while the remaining gaseous substances can be utilized further or sent to disposal. The methacrylic ester condensate from the second water-cooled heat exchanger is then cooled in a water-cooled or brine-cooled heat exchanger to a temperature of less than 15° C., preferably about 8 to about 12° C. This cooling step can lead to the methacrylic ester formed having a significantly lower content of formic acid than would be the case without the corresponding cooling step. The cooled condensate is then transferred to a phase separator. Here, the organic phase (methacrylic ester) is separated from the aqueous phase. The aqueous phase which, as well as water, may also have a content of organic compounds, especially alkanol, from the distillation step may in principle be used further as desired. However, as already described above, it may be preferred to recycle this mixture of water and organic compounds back into the esterification process by feeding it into the first reaction tank.

The removed organic phase is fed into a scrubber. There, the methacrylic ester is scrubbed with demineralized water. The separated aqueous phase which comprises a mixture of water and organic compounds, especially alkanol, can in turn in principle be used further as desired. However, it is advantageous for economic reasons to recycle this aqueous phase back into the esterification step by feeding it, for example, into the first tank.

Since methacrylic esters have a strong tendency to polymerize, it is in many cases advantageous when care is taken in the esterification of methacrylic acid that such a polymerization is prevented.

In plants for preparing methacrylic acid or methacrylic esters, polymerization often takes place when methacrylic acid or methacrylic ester firstly have a low flow rate, so that local calm zones can form, in which contact lasting over a long period between methacrylic acid or methacrylic ester and a polymerization initiator can be established, which can subsequently lead to polymerization.

In order to prevent such polymerization behaviour, it may be advantageous to optimize the substance flow to the effect that, firstly, the flow rate of the methacrylic ester or of the methacrylic acid is sufficiently high at substantially all points in the system that the number of calm zones is minimized. Furthermore, it may be advantageous to admix the stream of methacrylic acid or methacrylic ester with suitable stabilizers such that polymerization is largely suppressed.

For this purpose, the streams in the process presented here can in principle be admixed with stabilizers such that a minimum level of polymerization takes place in the system itself. To this end, the part of the plant in particular in which the methacrylic acid or the methacrylic ester is present in high concentration during or after the distillation is supplied with appropriate stabilizers.

For example, it has been found to be viable to supply a stabilizer at the top of the distillation column to the stream of methacrylic ester drawn off there. Furthermore, it has been found to be advantageous to flush those parts of the plant in which methacrylic acid or methacrylic ester is circulated with a temperature of more than about 20° C., preferably with a temperature in the range of about 20 to about 120° C., with a solution of stabilizer in methacrylic ester. For example, some of the condensate obtained in the heat exchangers, together with a suitable stabilizer, is recycled into the top of the distillation column such that the column top, on its interior, is sprayed constantly with stabilized methacrylic ester or stabilized methacrylic acid. This is preferably done in such a way that no calm zones can form in the top of the column, at which there is a risk of polymerization of methacrylic acid or methacrylic ester. The heat exchangers themselves may correspondingly likewise be charged with a stabilized solution of methacrylic acid or methacrylic ester in such a way that no calm zones can form here either.

It has also been found to be advantageous in the process presented here when, for example, the offgases comprising carbon monoxide from preceding processes, especially from the amidation step, are passed through the esterification plant together with steam. In this way, the gas mixture is once again purified to remove compounds which can be removed in solid or in liquid form. Secondly, these are collected at a central point and can be sent to further utilization or disposal.

The methacrylic ester obtained or the MMA obtained in the esterification and the subsequent prepurification, or the methacrylic acid obtained, are subsequently sent to a further treatment. The esterification results in dilute sulphuric acid as the remaining residual substance, which can likewise be sent to a further utilization.

Prepurification of the Ester or of the Acid

In the process presented here, the subject matter of the present invention can also be used in connection with a process for prepurifying methacrylic acid or methacrylic ester, as described in the process element which follows. For instance, in principle, crude methacrylic acid or a crude methacrylic ester can be subjected to a further purification in order to arrive at a very pure product. Such a purification which constitutes a further process element can, for example, be in one stage. However, it has been found to be advantageous in many cases when such a purification comprises at least two stages, in which case the low-boiling constituents of the product are removed in a first prepurification as described here. To this end, crude methacrylic ester or crude methacrylic acid is transferred first into a distillation column in which the low-boiling constituents and water can be removed. To this end, the crude methacrylic ester is sent to a distillation column, in which case the addition is performed, for instance, in the upper half of the column. The column bottom is heated with steam, for example, in such a way that a wall temperature of about 50 to about 120° C. is achieved. The purification is performed under reduced pressure. The pressure within the column in the case of the ester is preferably about 100 to about 600 mbar. The pressure within the column in the case of the acid is preferably about 40 to about 300 mbar.

At the top of the column, the low-boiling constituents are removed. In particular, these may, for example, be ether, acetone and methyl formate. The vapours are then condensed by means of one or more heat exchangers. For example, it has been found to be useful in some cases first to perform a condensation by means of two water-cooled heat exchangers connected in series. However, it is equally possible to use only one heat exchanger at this point. The heat exchangers are preferably operated in an upright state to increase the flow rate and in order to prevent the formation of stationary phases, preference being given to obtaining maximum wetting. Connected downstream of the water-cooled heat exchanger or the water-cooled heat exchangers may be a brine-cooled heat exchanger, but it is also possible to connect a battery of two or more brine-cooled heat exchangers downstream. In the battery of heat exchangers, the vapours are condensed, provided with stabilizer and, for example, fed to a phase separator. Since the vapours may also contain water, any aqueous phase which occurs is disposed of or sent to a further utilization. An example of a possible further utilization is recycling into an esterification reaction, for example into an esterification reaction as has been described above. In this case, the aqueous phase is preferably recycled into the first esterification tank.

The removed organic phase is fed as reflux into the top of the column. Some of the organic phase can in turn be used to spray the tops of the heat exchangers and the top of the column. Since the removed organic phase is a phase which has been admixed with stabilizer, it is thus possible firstly to effectively prevent the formation of calm zones. Secondly, the presence of the stabilizer brings about further suppression of the polymerization tendency of the vapours removed.

The condensate stream obtained from the heat exchangers is additionally preferably admixed with demineralized water in such a way that sufficient separating action can be achieved in the phase separator.

The gaseous compounds which remain after the condensation in the heat exchanger battery may, preferably by means of steam ejectors as reduced-pressure generators, be subjected once again to a condensation by means of one or more further heat exchangers. It has been found to be advantageous for economic reasons when such a postcondensation condenses not only the gaseous substances from the prepurification. For example, it is possible to feed further gaseous substances to such a postcondensation, as obtained from the main purification of methacrylic esters. The advantage of such a procedure lies, for example, in transferring such a proportion of methacrylic ester which has not been condensed in the main purification stage once more via the phase separator into the purification column in the prepurification. It is thus ensured, for example, that a maximization of yield can take place and minimum losses of methacrylic esters occur. Moreover, the suitable selection of the design and the operation of these further heat exchangers allows the composition of the offgas leaving these heat exchangers, especially the content of low boilers, to be adjusted.

Owing to the feeding of water in the prepurification of the methacrylic ester, the water content in the esterification and the concentration of low-boiling constituents in the crude methyl methacrylate overall can rise continuously. In order to prevent this, it may be advantageous to discharge some of the water fed to the system out of the system, preferably continuously. This discharge can in principle be effected, for example, in an order of magnitude in which water is fed to the system in the prepurification. The aqueous phase separated out in the phase separator typically has a content of organic constituents. It may therefore be advantageous to feed this water to a form of disposal which utilizes this content of organic substances.

For example, it may be advantageous when water thus contaminated with organic substances is fed to the combustion chamber in a sulphuric acid cleavage process. Owing to the oxidizable constituents, its calorific value can still be utilized at least partly. In addition, a possibly expensive disposal of the water contaminated with organic substances is thus often avoided.

Fine Purification of the Methacrylic Ester

For the fine purification of the methacrylic ester, the crude prepurified methacrylic ester is subjected to another distillation. This frees the crude methacrylic ester of its high-boiling constituents with the aid of a distillation column to obtain a pure methacrylic ester. To this end, the crude methacrylic ester is introduced into a distillation column, sometimes into the lower half, in a manner known to those skilled in the art.

The distillation column can in principle correspond to any design which appears to be suitable to those skilled in the art. However, it has been found to be advantageous in many cases for the purity of the resulting product when the distillation column is operated with one or more packings which correspond approximately to the following requirements:

Firstly, just like in the other lines flowed through by methacrylic ester, a minimum level of so-called "dead spaces" should form in the columns. The dead spaces lead to a comparatively long residence time of the methacrylic esters, which promotes their polymerization. This in turn leads to expensive production shutdowns and cleaning of the appropriate parts blocked with polymer. One way of countering the formation of dead spaces is, both by design and by a sufficient operating mode of the columns, to always load them with a sufficient amount of liquid, so that constant flushing of the columns and especially of the column internals such as packings is achieved. For instance, the columns may have spray devices which are designed for the spraying of the column internals. In addition, the column internals may be connected to one another such that barely any dead spaces, or better none at all, form. To this end, the column internals may be connected to one another or to the column via interrupted adhesion seams. Such adhesion seams have at least about 2, preferably at least about 5 and more preferably at least about 10 interruptions for 1 m of adhesion seam length. The length of these interruptions may be selected such that they make up at least about 10%, preferably at least about 20% and more preferably at least about 50%, but generally not more than 95% of the adhesion seam length. Another design measure may be that, in the internal regions of the column, especially those which come into contact with the methacrylic esters, less than about 50%, preferably less than about 25% and more preferably less than about 10% of all surfaces, especially of column internals, run horizontally. For example, the stubs which open into the interior of the column may be configured conically or with oblique surfaces. Another measure may consist in keeping the amount of liquid methacrylic ester present in the column bottom as low as possible during the operation of the column, and secondly in preventing overheating of this amount in spite of moderate temperatures and large evaporation surfaces during the evaporation. It may be advantageous in this context that the amount of liquid in the column bottom makes up in the range of about 0.1 to 15% and preferably about 1 to 10% of the total amount of methacrylic ester in the column. The measures proposed in this paragraph may also find use in the distillation of methacrylic acid.

In the purification of the methacrylic ester, its high-boiling constituents are separated from the product by distillation. To this end, the column bottom is heated with steam. The bottom temperature is preferably about 50 to about 80° C., in particular about 60 to about 75° C., with wall temperature of less than about 120° C.

The material obtained in the column bottom is preferably removed continuously and cooled by means of a heat exchanger or a battery of several heat exchangers to a temperature in a range of about 40 to about 80° C., preferably about 40 to about 60° C. and more preferably in a range of about 50 to 60° C.

This material, which comprises predominantly methacrylic ester, hydroxyisobutyric ester, methacrylic acid and stabilizer components, is subsequently, via a storage vessel, for example, disposed of or sent to another use. It has been found to be advantageous in many cases when the material obtained in the column bottom is recycled into the esterification reaction. For example, the material from the column bottom is recycled into the first esterification tank. This gives rise to the advantage that, with a view to a very economically viable method and a very high yield, relatively high-boiling compounds present in the column bottoms are recycled into the esterification reaction.

At the top of the column, the methacrylic ester purified by distillation is withdrawn and cooled by means of a heat exchanger or a battery of two or more heat exchangers. The heat of the vapours can be removed by means of water-cooled heat exchangers or by means of brine-cooled heat exchangers or by means of a combination of the two. It has been found to be useful in some cases when the vapours from the distillation column are transferred into two or more heat exchangers connected in parallel, which are operated by means of water cooling. The uncondensed fractions from the water-cooled heat exchangers can, for example, be introduced into a brine-cooled heat exchanger or a battery of two or more brine-cooled heat exchangers, which may be arranged in series or in parallel. The condensates obtainable from the heat exchangers are introduced into a collecting vessel and sent to a buffer vessel by means of a pump via a further heat exchanger or a battery of two or more further heat exchangers. The condensate stream is cooled, for example, by means of a battery of one or two water-cooled heat exchangers and one or two brine-cooled heat exchangers down to a temperature in a range of about 0 to about 20° C., preferably about 0 to about 15° C. and more preferably in a range of about 2 to 10° C.

A part-stream is withdrawn from the condensate stream and is recycled into the distillation column via the top of the column. The condensate stream can be fed into the top of the column in principle in any way, for example via distributors. However, it may be advantageous when a portion of the condensate stream is fed into the vapour line above the top of the column, for example sprayed in. It is also preferred that this feeding also introduces stabilizer into the top of the column.

A further part-stream of the condensate intended for recycling into the column can, for example, be branched off into the vapour line before introduction and be introduced directly into the top of the column. Here too, it is preferred that this feeding introduces stabilizer into the top of the column. The introduction into the top of the column can be done, for example, in such a way that the interior of the top of the column is sprayed with the condensate such that no calm zones can form in the top of the column at which the methacrylic ester can polymerize. It may additionally be advantageous to add a stabilizer for preventing polymerization to a condensate part-stream which is recycled into the column. This can be done, for example, by adding an appropriate amount of polymerization inhibitor as stabilizer to the condensate part-stream intended for spraying of the top of the column. It has been found to be advantageous in some cases when the condensate part-stream, after the addition of the stabilizer but before entry into the top of the column, passes through a suitable mixing apparatus, preferably a static mixer, in order to achieve very uniform distribution of the stabilizer in the condensate part-stream.

The uncondensable gaseous substances which are obtained in the purification process are, for example, sent to disposal.

The crude product present in the buffer vessel is kept with the aid of a brine cooler at a temperature of about 0 to about 20° C., preferably about 0 to about 15° C. and more preferably in a range of about 2 to 10° C.

In order to remove any further impurities from the product and to arrive at ultrapure alkyl methacrylates, the product can also be subjected to an absorptive purification stage. It has been found to be useful, for example, when the pure product as a whole, or at least a portion of the pure product, is purified further with the aid of a molecular sieve. Particularly acidic impurities, especially formic acid formed in the preparation process, can thus be removed in a simple manner from the product stream. It has additionally been found to be useful in some cases when the product stream, after passing through the adsorptive purification stage, also passes through one or more filters in order to remove any solids present in the product.

The streams obtained in the workup comprise predominantly polymerizable compounds. In order to, as already described more than once in this text, prevent the formation of calm zones, it has been found to be advantageous in the case of the process described here too when the parts of the plant which come into contact with methacrylic ester are constantly flowed over with methacrylic ester. In a further embodiment of the process presented here, a part-stream of methacrylic ester is therefore withdrawn downstream of the buffer vessel but upstream of the adsorptive purification stage in order to be flushed over the top regions of those heat exchangers which take up the vapours stemming from the distillation column.

The product obtained in the purification stage is subsequently withdrawn from the purification stage with a temperature in a range of about −5 to about 20° C., preferably about 0 to about 15° C. and more preferably in a range of about 2 to 10° C.

Stripping of the Consumed Acid

In the process presented here, it may be advisable, for example, in a further process element, to subject the consumed sulphuric acid obtained in the process to a purification in order to subsequently recycle it back into the process. In this case, for example, a stream comprising consumed sulphuric acid, as can be obtained from the esterification, can be contacted with steam in a flotation vessel. As this is done, at least some of the solids present can be deposited on the surface of the liquid, and these deposited solids can be separated out. The vapours are subsequently condensed in a heat exchanger, preferably with water cooling, cooled and recycled into the esterification reaction.

It has been found to be advantageous in some cases when corrosion is prevented in the heat exchangers and the cooling action is improved further by introducing a mixture of water and organic compounds, as obtained by scrubbing in the course of the esterification in the purification of the methacrylic ester prepared, into the heat exchangers in such a way that the tops of the heat exchangers are sprayed with this mixture. In addition to the corrosion-reducing action and the cooling of the acid in the heat exchanger, this procedure has a further advantage. Material which stems from the esterification (a mixture of water and predominantly methanol) is recycled into the esterification process together with the methacrylic acid and methacrylic ester stemming from exactly this process. In the stripper, the above-described flotation affords mixtures of acid and solids. After their removal, these are sent to any further use or to disposal. It is possible, for example, to incinerate the resulting mixture in a cleavage plant and hence to obtain sulphuric acid again and in order to recover some of the energy used in the process.

The uncondensable gaseous compounds obtained in the stripping are sent to any further use or disposed of.

The plant described here for removing solids from the consumed acid and for recycling material from the esterification process into exactly this process can also be performed, for example, twice for reasons of operational reliability. For instance, the two or more flotation vessels can be used offset in time. Since solids can settle out in these vessels, it is advantageous to remove them when the particular flotation vessel is not being used.

Figure 2:
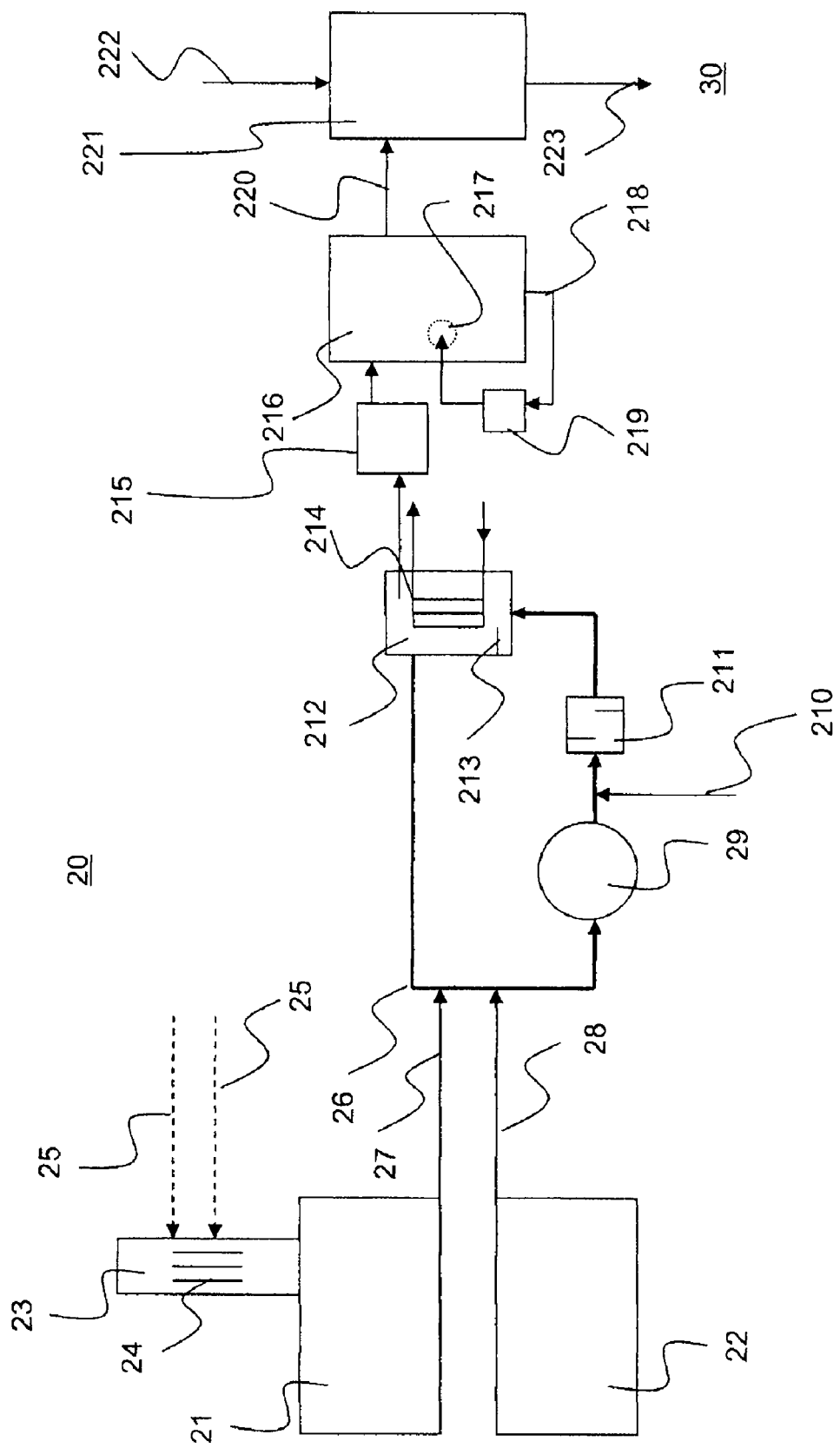
Figure 3:
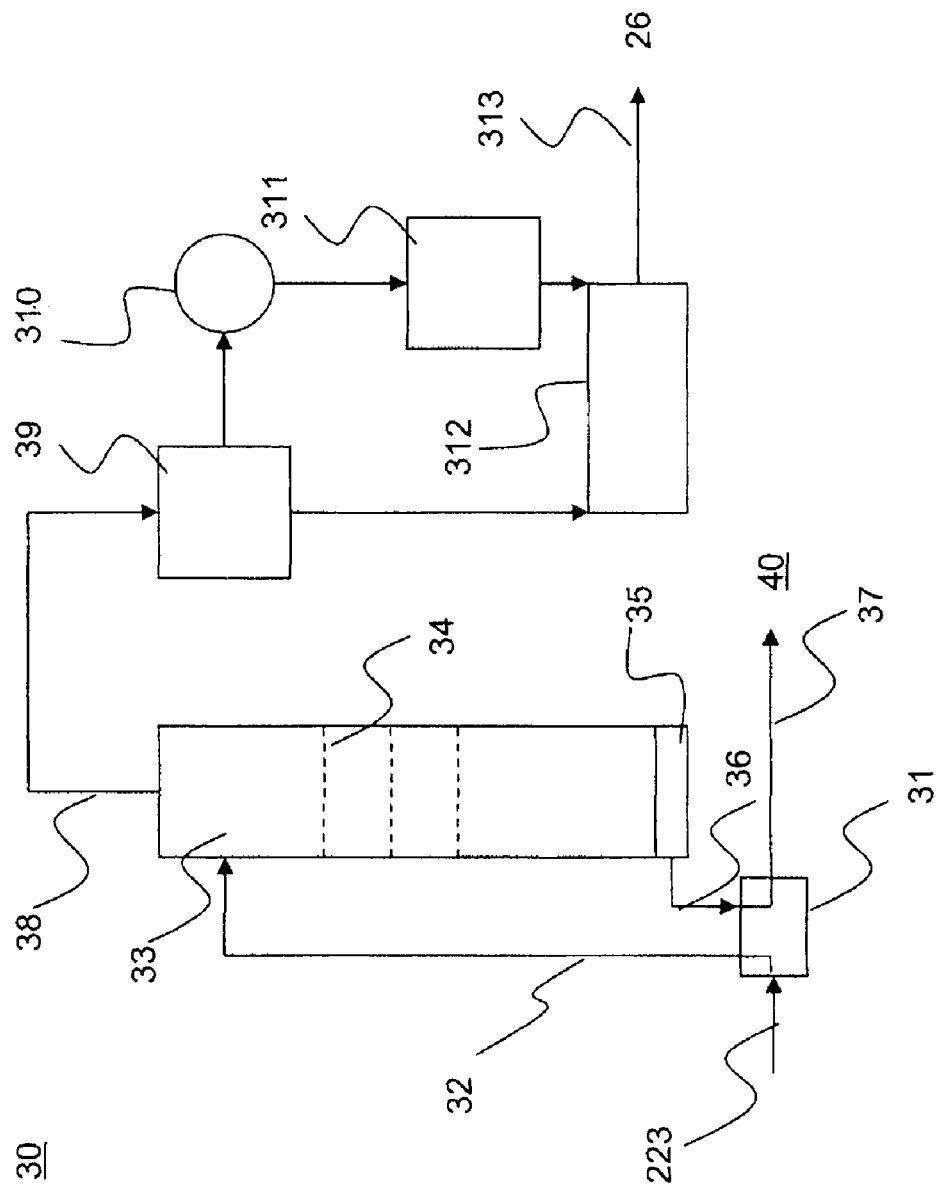
Figure 4:
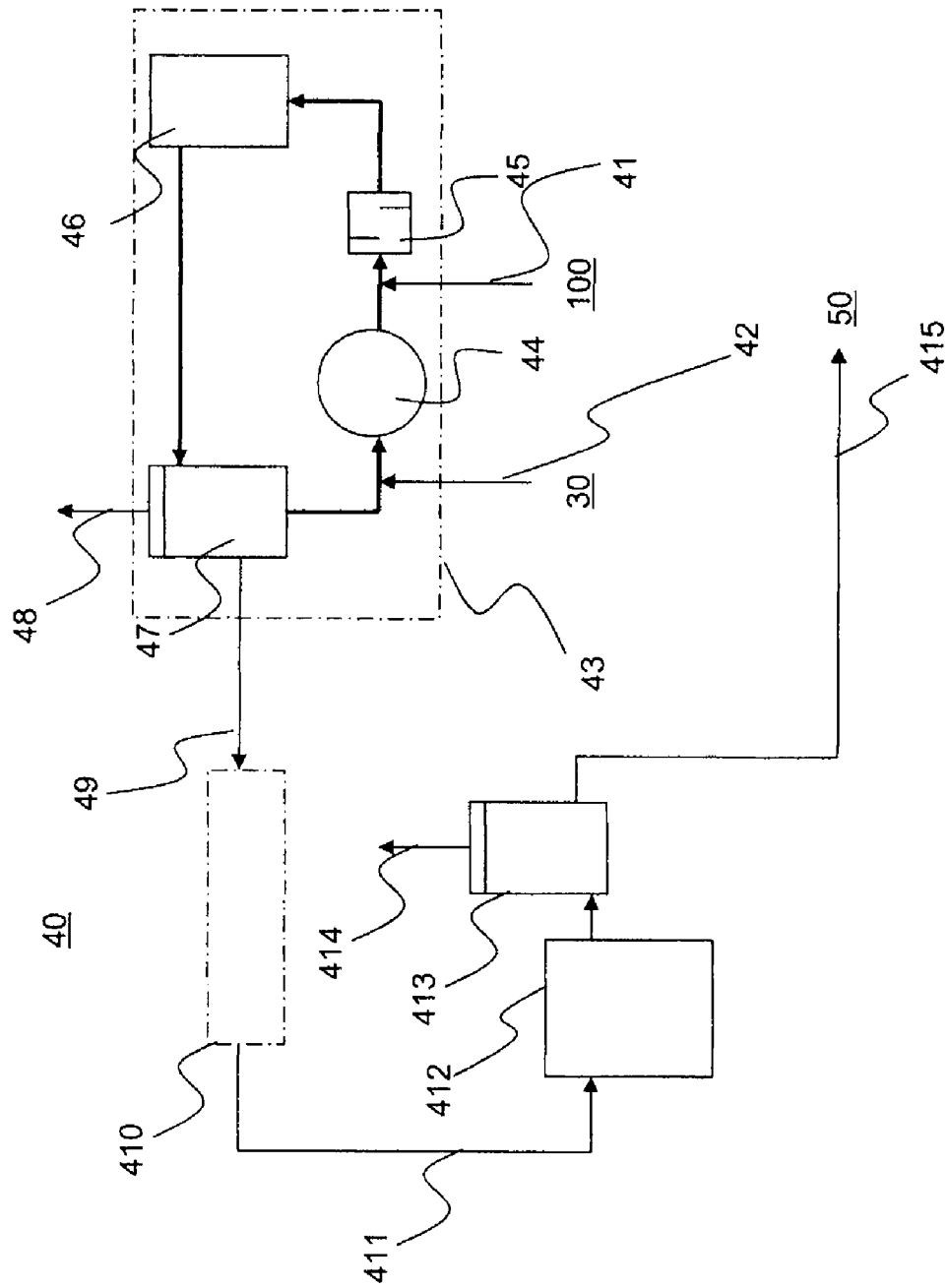
Figure 5:
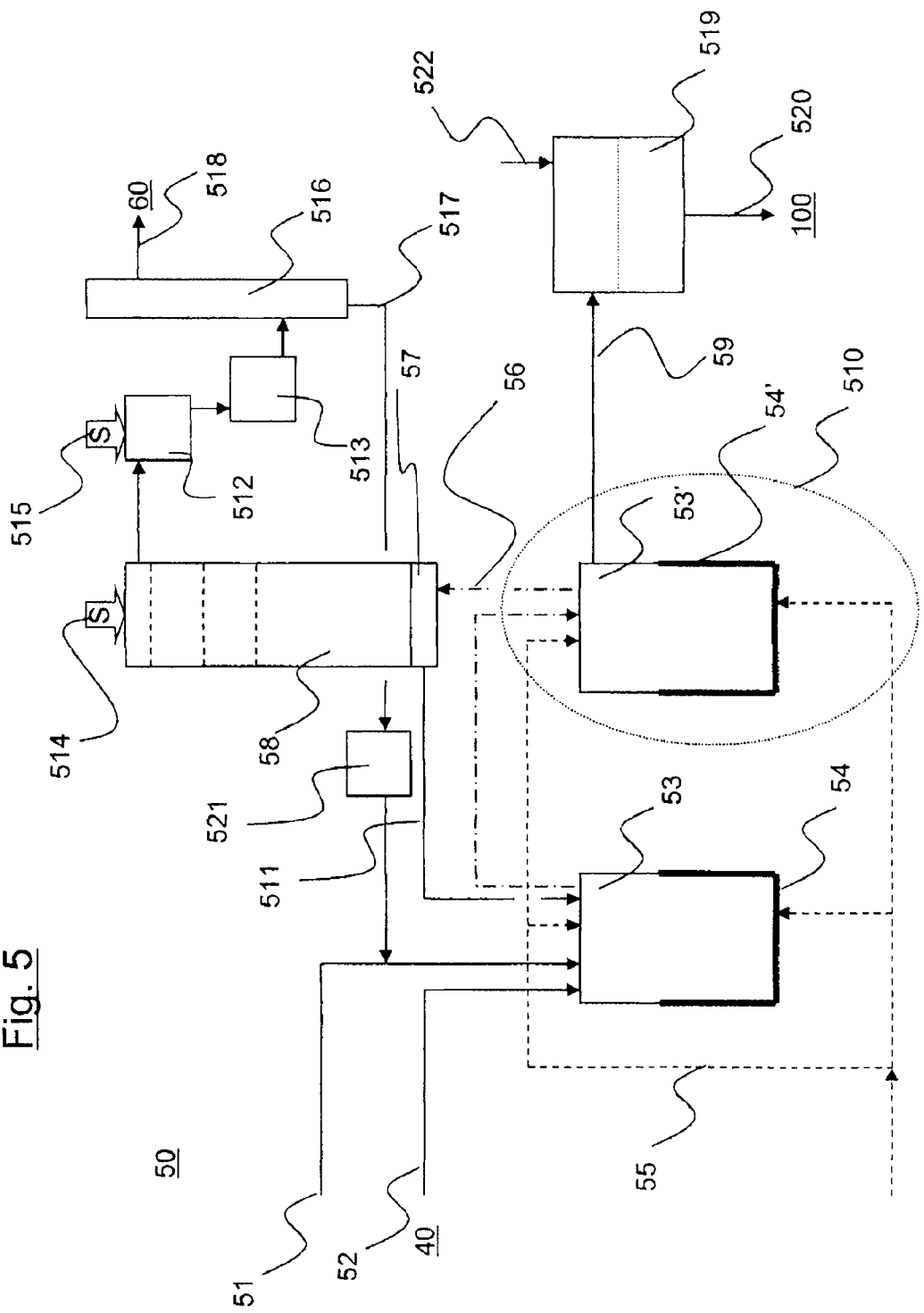
Figure 6:
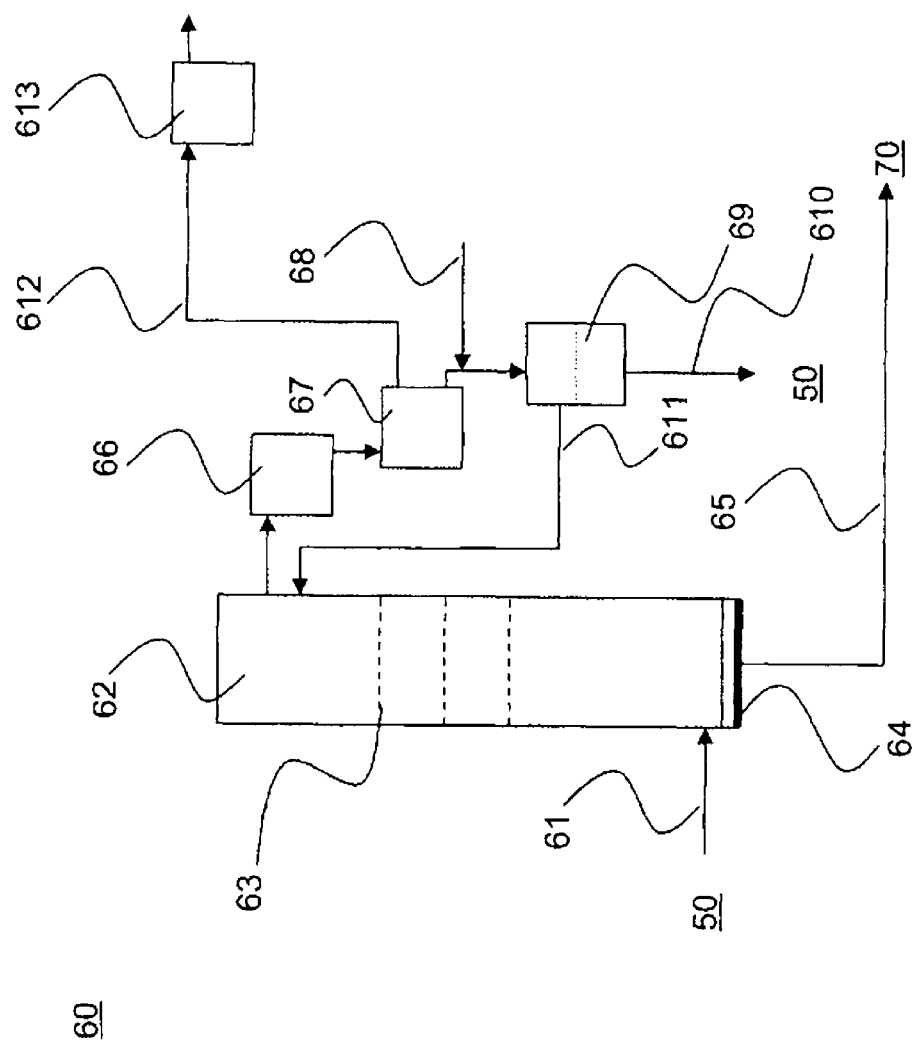
Figure 7:
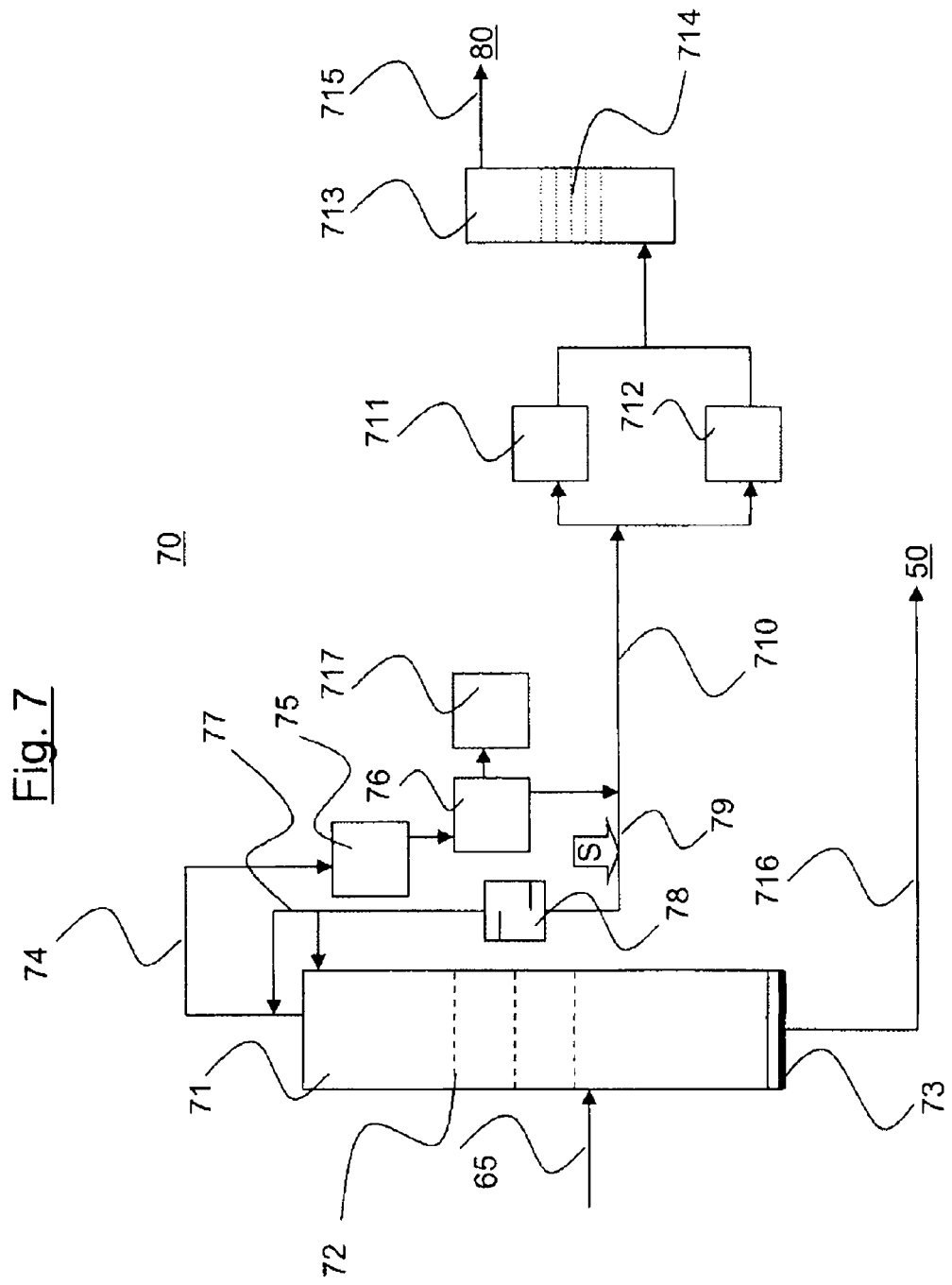
Figure 8:
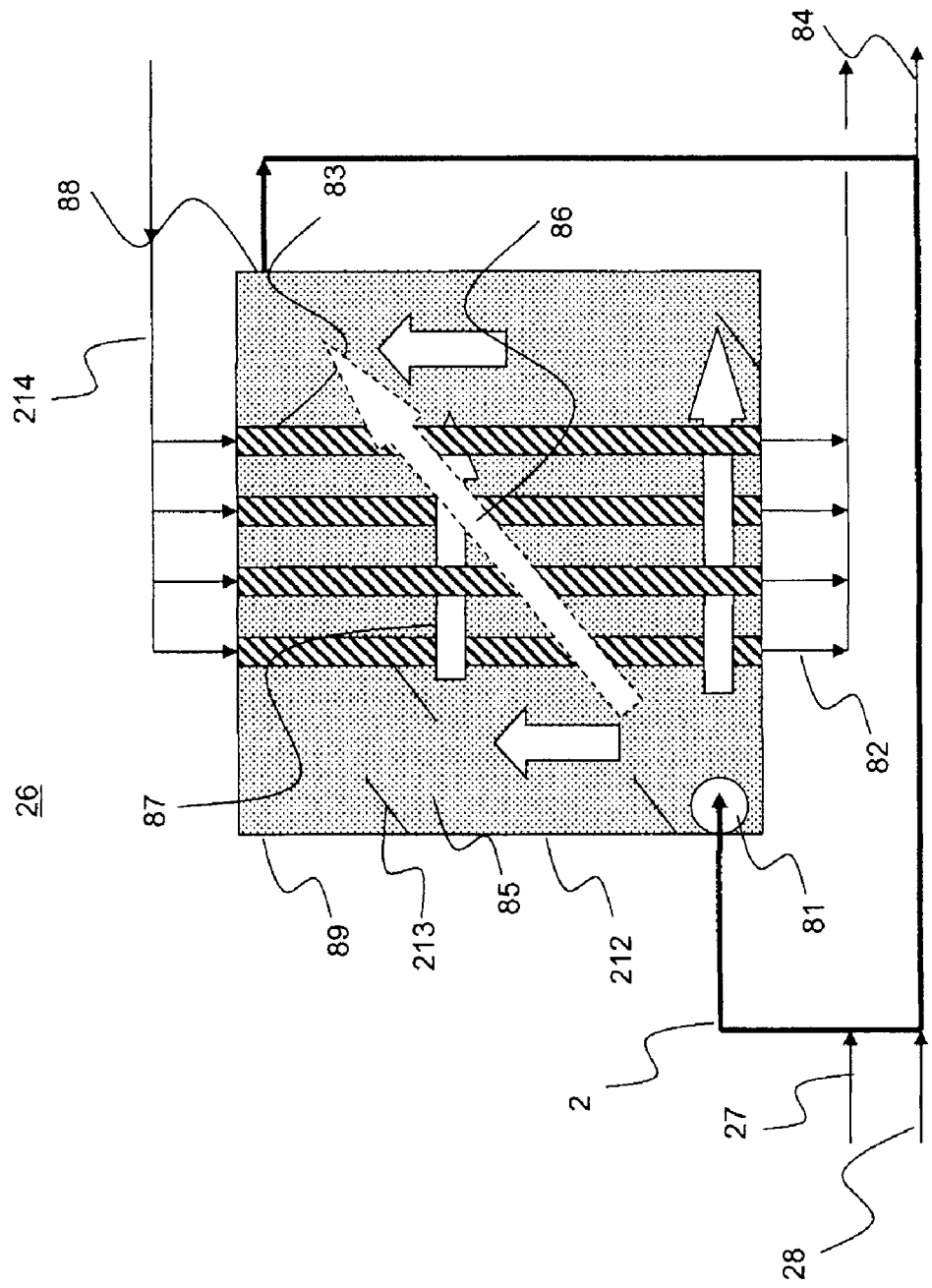

The aforementioned will now be illustrated in detail with reference to nonlimiting drawings and examples. The schematic drawings show:

FIG. 1: a plant system for preparing and processing methacrylic acid or methyl methacrylate, FIG. 2: a plant for preparing acetone cyanohydrin, FIG. 3: a workup plant for acetone cyanohydrin, FIG. 4: an amidation plant, FIG. 5: an esterification plant, FIG. 6: a plant for prepurifying the ester, FIG. 7: a fine purification plant for the ester, FIG. 8: a heat exchanger as part of the plant for preparing acetone cyanohydrin.

FIG. 1 shows the preferred elements of a plant system 1 for preparing methacrylic acid or methacrylic esters and their further processing products. The plant system 1 has various plants connected to one another usually in a fluid-conducting manner as elements of this system. This plant system includes acetone cyanohydrin preparation 20, followed by acetone cyanohydrin workup 30, followed by an amidation 40, followed by an esterification/hydrolysis 50/50a, followed by a workup for ester or methacrylic acid 60, followed in turn by a fine purification 70, after which the ester, usually methyl methacrylate, or methacrylic acid is present. The pure ester/pure acid thus obtained can be sent to a further processing plant 80. Useful further processing plants 80 include in particular polymerization apparatus and reactors for further organic reactions. In the polymerization reactors, polymethacrylates can be prepared, and, in the reactors for organic reactions, the pure monomers obtained here can be converted to further organic compounds. The further processing plant or the further processing plants 80 is/are followed by a finishing 90. When the further processing products are polymers of methacrylic acid or methacrylic esters, especially methyl methacrylate, they are processed further to give fibres, moulding compositions, especially granules, films, slabs, automobile parts and other mouldings by suitable equipment such as extruders, blown-film extruders, injection-moulding machines, spinneret dies and the like. In addition, the plant system 1 in many cases comprises a sulphuric acid plant 100. For this plant, all sulphuric acid plants which appear to be suitable for this purpose to the person skilled in the art are useful in principle. Reference is made in this context, for example, to Chapter 4, page 89 ff. in "Integrated Pollution Prevention and Control—Draft Reference Document on Best Available Techniques for the Manufacture of Large Volume Inorganic Chemicals—Amino Acids and Fertilizers" obtainable via the European Commission. The sulphuric acid plant 10 is connected to a series of other plants. For instance, the acetone cyanohydrin preparation 20 is supplied with concentrated sulphuric acid via a sulphuric acid line 2. Moreover, a further sulphuric acid line 3 exists between the sulphuric acid plant 100 and the amidation 40. The dilute sulphuric acid also referred to as "Spent Acid" from the esterification 50 (hydrolysis 50a) is transferred to the sulphuric acid plant 100 through the lines for spent sulphuric acid 4 and 5. In the sulphuric acid plant 100, the dilute sulphuric acid can be worked up. The workup of the dilute sulphuric acid can be effected, for example, as described in WO 02/23088 A1 or WO 02/23089 A1. In general, the plants are manufactured from the materials which are familiar to those skilled in the art and appear to be suitable for the particular stresses. Usually, the material is stainless steel which must in particular have exceptional acid resistance. The regions of the plants which are operated with sulphuric acid and especially with concentrated sulphuric acid are additionally lined and protected with ceramic materials or plastics. In addition, the methacrylic acid obtained in the methacrylic acid plant 50a can be fed via a methacrylic acid line 6 to the prepurification 60. It has also been found to be useful to add a stabilizer indicated with "S" in the acetone cyanohydrin preparation 20, the amidation 40, the esterification 50, the hydrolysis 50a, the prepurification 60 and also the end purification 70.

In the acetone cyanohydrin preparation 20 shown in FIG. 2, the acetone is provided in an acetone vessel 21 and the hydrocyanic acid in a hydrocyanic acid vessel 22. The acetone vessel 21 has a scrubbing tower 23 which, in its upper region, has one or more cooling elements 24. A series of offgas lines 25 which stem from various plants in the plant system 1 open into the scrubbing tower 23. The acetone is fed into a loop reactor 26 via the acetone feed 27 and the hydrocyanic acid via the hydrocyanic acid feed 28. Downstream of the hydrocyanic acid feed 28 is disposed a pump 29, followed in turn by a catalyst feed 210 which is followed by a static mixer 211. This is followed by a heat exchanger 212 which has a series of flow resistances 213 and at least one cooling line 214. In the loop reactor 26, the reaction mixture consisting of acetone, hydrocyanic acid and catalyst is conducted in a circuit to a considerable degree, which is indicated by bold lines. From the heat exchanger 212, the reaction mixture is conducted via the flow resistances along the cooling lines 214, and a portion of the circulation stream is passed into a further heat exchanger 215 to which is connected a collecting vessel 216 in which a nozzle 217 is present as part of a cooling circuit 218 with a heat exchanger 219, which keeps the reaction product firstly in motion and secondly cool. Via an outlet 220 which follows the collecting vessel 216, a stabilizer vessel 221 is attached, into which a sulphuric acid feed 222 opens and from which the crude acetone cyanohydrin is conducted through the outlet 223 into the acetone cyanohydrin workup 30.

In FIG. 3, coming from the cyanohydrin preparation 20, the outlet 223 opens into a heat exchanger 31 in which the stream coming from the cyanohydrin preparation 20 is heated. A vapour feed 32 is connected to the heat exchanger 31 and opens out in the upper region, preferably the top region, of a column 33. The column 33 has a multitude of packings 34 which are usually configured as trays. In the lower region of the column 33 is disposed the column bottom 35 from which a bottoms outlet 36 leads into the heat exchanger 31 and heats the streams conducted through the outlet 223 into the heat exchanger 31. A pure product line 37 is connected to the heat exchanger 31, which is followed downstream by the amidation 40. In the top region of the column 33 is disposed a tops outlet 38 which opens into a heat exchanger 39 to which a vacuum pump 310 is connected and opens in turn into a heat exchanger 311. Both the heat exchanger 39 and the heat exchanger 311 are connected via lines to a cooling vessel 312 to which a recycle line 313 is connected and is connected to the loop reactor 26 in the acetone cyanohydrin preparation 20.

The amidation 40 depicted in FIG. 4 first has an acetone cyanohydrin feed 41 and a sulphuric acid feed 42 which open into a loop reactor 43. The acetone cyanohydrin feed 41 connected to the acetone cyanohydrin workup 30 opens into the circuit of the loop reactor 43 downstream of a pump 44 and upstream of a mixer 45. Upstream of this pump 44, the sulphuric acid feed 42 opens out. The mixer 45 is followed downstream by a heat exchanger 46 which in turn opens into a gas separator 47 from which, firstly, a gas outlet 48 and a feed 49 to a further loop reactor 410 exit. The further loop reactor 410 or a third has a comparable construction to the first loop reactor 43. From the further loop reactor 410, a feed 411 enters a heat exchanger 412 which is followed by a gas separator 413, from which, firstly, a gas outlet 414 and an amide line 415 exit, the latter leading to the esterification/hydrolysis 50/MAA plant 50a.

FIG. 5 shows the esterification 50, in which a solvent line 51 which conducts water and organic solvent, and an amide line 52 connected to the amidation 40 open into a tank 53 which is heatable by a tank heater 54. In addition, an alcohol line 55 shown with a broken line opens into the tank 53. The alcohol line 55 opens out both in the upper and in the lower region of the tank 53. The first tank 53 is connected to a further tank 53', which has a further tank heater 54', via an ester vapour line 56 indicated by a line of dashes and dots. This further tank 53' too is connected to the alcohol line 55 both from the bottom and from the top. The ester vapour line 56 is connected to the upper region of the tank 53' and opens into a bottom 57 of a column 58. In addition, a line for dilute sulphuric acid 59 is present in the upper region of the tank 53'. A tank unit 510 encircled in a dotted ellipse is formed from a heatable tank 53 and 54 with alcohol line 55 and ester vapour line 56. It is possible for one, two or more of such tank units to follow in battery-like succession, each of these tank units 510 being connected via the ester vapour line 56 to the bottom 57 of the column 58. From the bottom 57 of the column 58, a high boiler line 511 also leads to the tank 53, in order to feed water and organic solvent back to the esterification. In the upper region, preferably the top, of the column 58, a first heat exchanger 512 followed by a further phase separator 513 are connected via a suitable line. Both at the top of the column 58 and in the first heat exchanger 512, a first stabilizer feed 514 (stabilizer indicated with "S") and a further stabilizer feed 515 may be provided in order to feed an inhibitor or stabilizer which prevents undesired polymerization. Connected to the further phase separator 513 is a scrubber 516 in whose lower region a solvent line 517 exits and opens out in the solvent line 51 via a heat exchanger 521. From the upper region of the scrubber 516, a crude ester line exits and opens into the ester workup 60. The spent acid line 59 exiting from the upper region of the tank 53' or of the tank of the last tank unit 510 opens into a flotation vessel 519 for removal of the solids and constituents insoluble in the spent acid. From the flotation vessel 519, a spent acid outlet 520 enters the sulphuric acid plant 100, and a low boiler vapour line 522 which conducts the low-boiling constituents, for further workup and recycling, enters the esterification.

The ester workup shown in FIG. 6 is connected to the esterification 50 via a crude ester line 61, the crude ester feed 61 opening into the middle region of a vacuum distillation column 62. This column 62 has column internals 63 and a bottom heater 64 arranged in the lower region of the column 62. From the lower region of the column 62 which constitutes the bottom of this column, an ester outlet 65 exits, opens into the ester fine purification 70 and hence feeds the crude ester freed of low boilers to the fine purification. In the upper region of the column 62, usually in the top, a first heat exchanger 66 is connected via an outlet, as are one further heat exchanger or a plurality of heat exchangers 67 which are followed by a phase separator 69. In the phase separator 69, the stream 68 and the mixture stemming from the heat exchanger 67 is divided into organic and aqueous constituents, a recycle line 611 in the upper region being connected to the phase separator 69 and opening out in the upper region of the column 62. In the lower region of the separator, a water outlet 610 is present and opens into the esterification 50 in order to feed the water removed back to the esterification. A reduced-pressure generator 613 is connected to the heat exchangers 66 and 67 via a reduced-pressure line 612.

In FIG. 7, the ester outlet 65 stemming from the ester workup 60 opens into a distillation column 71. This comprises a plurality of column internals 71 and, in the lower region of the distillation column 71, a column bottom heater 73. From the top region of the distillation column 71, a pure ester vapour line 74 enters a first heat exchanger 75 which is followed by one (or more) further heat exchangers 76 which are connected to a reduced-pressure generator 717. The outlet of the further heat exchanger 76 has a line from which, firstly, an ester recycle line 77 opens into the upper region, or into the top, of the distillation column 71. The ester recycle line 77 has a stabilizer metering point 79 which is disposed in the ester recycle line 77 upstream of a mixer 78. Secondly, from the line of the further heat exchanger 76, a pure ester outlet 710 exits. An additional heat exchanger 711 and another heat exchanger 712 are connected to this in series connection. These are followed by a molecular sieve vessel 713 which has molecular sieve packings 714. Purified further by the molecular sieve, the ultrapure ester is transferred through the ultrapure ester outlet connected to the molecular sieve vessel into the further processing plant 80.

FIG. 8 is a section from FIG. 2, so that reference is made to the figure description for FIG. 2. In addition: the reaction mixture is fed into a cooling region 85 bordered by a reaction mixture outlet 88 through an injecting element 81 configured as a nozzle. The cooling region 85 has a volume symbolized by the dotted area, which does not include the volumes of the multitude of cooling elements which are symbolized by the hatched areas and which are flowed through with coolant via the coolant inlet 214 and the coolant outlet 82. It is discernible from FIG. 8 that the volume of the cooling region symbolized by the dotted area is greater than the volume of the cooling elements symbolized by the hatched area. The deflecting elements or flow resistances 213 configured as baffle plates may be provided either at a cooler wall 89 surrounding the cooling region 85 or at the cooling elements 83. The arrangement and selection of the injecting elements 81 and of the deflecting elements 213 can achieve cooling flow directions 87 deviating from a main flow direction 86 shown by the dotted arrow, and hence bring about good mixing of the reaction mixture in the cooling region 85.

EXAMPLES

In a reaction arrangement corresponding to FIG. 8 with a loop reactor 26, HCN and acetone were reacted at 10° C. in the presence of diethylamine as a catalyst. The reaction conditions are shown in the table below.

| Example | Volume of cooling region 85 relative to outer volume of cooling elements 83 | Reaction conditions | Residence time in the heat exchanger 212 | Conversion of ACH |
|---|---|---|---|---|
| 1. | 1:1.7 | No flow resistances 213 | 0.2 h | 75% |
| 2. | 1:1.7 | Flow resistances 213 | 0.3 | 81% |
| 3. | 1:0.7 | No flow resistances 213 | 0.5 h | 83% |
| 4. | 1:0.7 | Flow resistances 213 | 0.6 | 87% |

| Reference numeral list | |
|---|---|
| 1 | Plant system |
| 2 | Sulphuric acid line |
| 3 | Further sulphuric acid line |
| 4 | Spent sulphuric acid line-ester |
| 5 | Spent sulphuric acid line-acid |
| 6 | Methacrylic acid line |
| 20 | Acetone cyanohydrin preparation |
| 30 | Acetone cyanohydrin workup |
| 40 | Amidation |
| 50 | Esterification |
| 50a | Hydrolysis |
| 60 | Prepurification |
| 70 | Fine purification |
| 80 | Further processing plant |
| 90 | Finishing |
| 100 | Sulphuric acid plant |
| 21 | Acetone vessel |
| 22 | Hydrocyanic acid vessel |
| 23 | Scrubbing tower |
| 24 | Cooling elements |
| 25 | Offgas lines |
| 26 | Loop reactor |
| 27 | Acetone feed |
| 28 | Hydrocyanic acid feed |
| 29 | Pump |
| 210 | Catalyst feed |
| 211 | Mixer |
| 212 | Heat exchanger |
| 213 | Flow resistance |
| 214 | Cooling lines |
| 215 | Heat exchanger |
| 216 | Collecting vessel |
| 217 | Nozzle |
| 218 | Cooling circuit |
| 219 | Heat exchanger |
| 220 | Outlet |
| 221 | Stabilizing vessel |
| 222 | Sulphuric acid feed |
| 223 | Outlet |
| 31 | Heat exchanger |
| 32 | Vapour feed |
| 33 | Column |
| 34 | Packings |
| 35 | Column bottom with heatexchanger |
| 36 | Bottoms outlet |
| 37 | Pure product line |
| 38 | Tops outlet |
| 39 | Heat exchanger |
| 310 | Vacuum pump |
| 311 | Heat exchanger |
| 312 | Cooling vessel |
| 313 | Recycle line |
| 41 | Acetone cyanohydrin feed |
| 42 | Sulphuric acid feed |
| 43 | Loop reactor |
| 44 | Pump |
| 45 | Mixer |
| 46 | Heat exchanger |
| 47 | Gas separator |
| 48 | Gas outlet |
| 49 | Feed |
| 410 | Further loop reactor |
| 411 | Feed |
| 412 | Heat exchanger |
| 413 | Gas separator |
| 414 | Gas outlet |
| 415 | Amide line |
| 51 | Solvent line |
| 52 | Amide line |
| 53 | First tank |
| 54 | First tank heater |
| 53' | Further tank |
| 54' | Further tank heater |
| 55 | Alcohol line |
| 56 | Ester vapour line |
| 57 | Column bottom |
| 58 | Column |
| 59 | Spent acid line |
| 510 | Tank unit |
| 511 | High boiler line |
| 512 | Heat exchanger |
| 513 | Phase separator |
| 514 | Stabilizer feed |
| 515 | Further stabilizer feed |
| 516 | Extraction column |
| 517 | Solvent line |
| 518 | Crude ester line |
| 519 | Flotation vessel |
| 520 | Spent acid outlet |
| 521 | Heat exchanger |
| 522 | Low boiler vapour line |
| 61 | Crude ester line |
| 62 | Vacuum distillation column |
| 63 | Column internals |
| 64 | Bottom heater |
| 65 | Ester outlet |
| 66 | Heat exchanger |
| 67 | Heat exchanger |
| 68 | Water feed |
| 69 | Phase separator |
| 610 | Water outlet |
| 611 | Recycle line |
| 612 | Reduced-pressure line |
| 613 | Reduced-pressure generator |
| 71 | Distillation column |
| 72 | Column internals |
| 73 | Column bottom heater |
| 74 | Pure ester vapour line |
| 75 | First heat exchanger |
| 76 | Further heat exchanger |
| 77 | Ester recycle line |
| 78 | Mixer |
| 79 | Stabilizer metering point |
| 710 | Pure ester outlet |
| 711 | Additional heat exchanger |
| 712 | Other heat exchanger |
| 713 | Molecular sieve vessel |
| 714 | Molecular sieve packings |
| 715 | Ultrapure ester outlet |
| 716 | High boiler line |
| 717 | Reduced-pressure generator |
| 81 | Injecting element |
| 82 | Coolant outlet |
| 83 | Cooling element |
| 84 | Product outlet |
| 85 | Cooling region |
| 86 | Main flow direction |
| 87 | Cooling flow direction |
| 88 | Reaction mixture outlet |
| 89 | Cooler wall |

The invention claimed is:

1. A process for preparing acetone cyanohydrin, comprising:
   A. contacting acetone and hydrocyanic acid in the absence of a metal cyanide composition in a reactor to give a reaction mixture, the reaction mixture being circulated, to obtain acetone cyanohydrin;
   B. cooling at least 70% by weight of the reaction mixture by flowing said at least 70% by weight of said reaction mixture through a cooling region of a cooler, the cooler including one cooling element or at least two cooling elements;
   wherein a residence time of the reaction mixture in the cooler is in a range of from 0.1 h to 2 h; and
   C. discharging at least a portion of the acetone cyanohydrin obtained from the reactor,
   wherein the volume of the cooling region of the cooler based on the total internal volume of the cooler is greater than the volume of the cooling element or of the at least two cooling elements of the cooler.

2. The process according to claim 1, wherein at least some of the reaction mixture flows in a cooler flow direction different from the main flow direction at least during the cooling.

3. The process according to claim 2, wherein the cooler flow direction is obtained by deflecting the reaction mixture.

4. The process according to claim 3, wherein the deflection is effected by a deflecting means provided in the cooler or connected to the cooler.

5. The process according to claim 4, wherein the deflecting means is an injecting element or a baffle element or both.

6. The process according to claim 4, wherein the deflecting means is provided in the cooling region.

7. The process according to claim 1, wherein the cooling element is an elongated hollow body which can be flowed through by coolant.

8. The process according to claim 7, wherein the cooling element has a rod-shaped or plate-shaped configuration.

9. The process according to claim 7, wherein the cooling element is a tube bundle.

10. The process according to claim 1, wherein the residence time of the reaction mixture in the cooler is in a range of about 720 to 5400 seconds.

11. A process for preparing an alkyl methacrylate, comprising:
   a. preparing an acetone cyanohydrin by a process according to claim 1;
   b. contacting the acetone cyanohydrin with an inorganic acid to obtain a methacrylamide;
   c. contacting the methacrylamide with an alcohol to obtain an alkyl methacrylate; and
   d. optionally purifying the alkyl methacrylate.

12. A process for preparing methacrylic acid, comprising:
   α) preparing an acetone cyanohydrin by a process according to claim 1;
   β) contacting the acetone cyanohydrin with an inorganic acid to obtain a methacrylamide; and
   γ) reacting the methacrylamide with water to give methacrylic acid.

13. A process for preparing polymers based at least partly on alkyl methacrylates, comprising:
   a) preparing an alkyl methacrylate by a process according to claim 11;
   b) polymerizing the alkyl methacrylate and optionally a comonomer; and
   c) working up the alkyl methacrylate.

14. The process according to claim 13, wherein the polymerization is effected by free-radical polymerization.

15. Fibres, films, coatings, moulding compositions, mouldings, papermaking auxiliaries, leather auxiliaries, flocculants and drilling additives which are based on an alkyl methacrylate obtainable by a process according to claim 11.

16. Fibres, films, coatings, moulding compositions, mouldings, papermaking auxiliaries, leather auxiliaries, flocculants and drilling additives which are based on a methacrylic acid obtainable by a process according to claim 12.

17. A process for preparing acetone cyanohydrin, comprising:
   A. contacting acetone and hydrocyanic acid in the absence of a metal cyanide composition in a loop reactor to give a reaction mixture, the reaction mixture being circulated in said loop reactor, to obtain acetone cyanohydrin;
   B. cooling at least 70% by weight of the reaction mixture by flowing said at least 70% by weight of said reaction mixture through a cooling region of a cooler, the cooler including one cooling element or at least two cooling elements;
   wherein said cooling region is part of said loop reactor;
   wherein a residence time of the reaction mixture in the cooler is in a range of from 0.1 h to 2 h; and
   C. discharging at least a portion of the acetone cyanohydrin obtained from the reactor,
   wherein the volume of the cooling region of the cooler based on the total internal volume of the cooler is greater than the volume of the cooling element or of the at least two cooling elements of the cooler; and
   wherein at least some of the reaction mixture flows in a cooler flow direction different from the main flow direction at least during the cooling.

* * * * *